United States Patent
Hashimoto et al.

(10) Patent No.: US 9,402,969 B2
(45) Date of Patent: Aug. 2, 2016

(54) SPUTUM ASPIRATING APPARATUS, ARTIFICIAL VENTILATION SYSTEM INCLUDING A SPUTUM ASPIRATING APPARATUS, AND METHOD FOR OPERATING A SPUTUM ASPIRATING APPARATUS

(71) Applicants: Ulvac Kiko, Inc., Miyazaki (JP); Medicalseed Co., Ltd., Miyazaki (JP)

(72) Inventors: Yasuhiro Hashimoto, Miyazaki (JP); Shingo Takesawa, Miyasaki (JP)

(73) Assignees: ULVAC KIKO, INC., Miyazaki (JP); MEDICALSEED CO., LTD., Miyazaki (JP)

( * ) Notice: Subject to any disclaimer, the term of this patent is extended or adjusted under 35 U.S.C. 154(b) by 0 days.

(21) Appl. No.: 14/403,748

(22) PCT Filed: Sep. 17, 2013

(86) PCT No.: PCT/JP2013/005478
§ 371 (c)(1),
(2) Date: Nov. 25, 2014

(87) PCT Pub. No.: WO2014/050013
PCT Pub. Date: Apr. 3, 2014

(65) Prior Publication Data
US 2015/0190598 A1    Jul. 9, 2015

(30) Foreign Application Priority Data
Sep. 26, 2012   (JP) .................................. 2013-212886

(51) Int. Cl.
*A61M 16/00*    (2006.01)
*A61M 16/04*    (2006.01)
(Continued)

(52) U.S. Cl.
CPC ....... *A61M 16/0463* (2013.01); *A61M 16/0003* (2014.02); *A61M 16/0009* (2014.02);
(Continued)

(58) Field of Classification Search
CPC ..................... A61M 16/0463; A61M 16/0477; A61M 16/0009; A61M 16/0486; A61M 16/201; A61M 2016/0027; A61M 2016/003; A61M 2202/0014
See application file for complete search history.

(56) References Cited

U.S. PATENT DOCUMENTS

| 2,900,978 A | * | 8/1959 | Johannisson ....... A61M 1/0076 417/174 |
| 5,125,893 A | * | 6/1992 | Dryden ............. A61M 16/0463 128/207.14 |

(Continued)

FOREIGN PATENT DOCUMENTS

| JP | 2002-519122 A | 7/2002 |
| JP | 2005-027879 A | 2/2005 |

(Continued)

OTHER PUBLICATIONS

International Search Report in International Application No. PCT/JP2013/005478, filed Sep. 17, 2013.

*Primary Examiner* — Lynne Anderson
*Assistant Examiner* — Kathryn E Ditmer
(74) *Attorney, Agent, or Firm* — Saliwanchik, Lloyd & Eisenschenk

(57) ABSTRACT

To provide a sputum aspirating apparatus capable of automatically aspirating sputum safely. a sputum aspirating apparatus includes a suction line, a switching unit, a measurement unit, and a control unit. The suction line has a suction inlet which aspirates sputum produced in patient's respiratory tract; and an accommodating part maintained at negative pressure, which accommodates the aspirated sputum. The switching unit is in the suction line, and can switch between first state where the suction inlet communicates with the accommodating part, and second state where the suction inlet is shutoff from the accommodating part. The measurement unit measures the expired air being aspirated into the accommodating part, under the first state. The control unit can switch the switching unit from the second state to the first state during expiration, and keep the first state when the expired air measured by the measurement unit is under a predetermined value.

8 Claims, 13 Drawing Sheets

(51) Int. Cl.
 *A61M 1/00* (2006.01)
 *A61M 16/20* (2006.01)
 *A61M 16/10* (2006.01)
 *A61M 16/08* (2006.01)

(52) U.S. Cl.
 CPC ......... *A61M16/0069* (2014.02); *A61M 1/0031* (2013.01); *A61M 16/0051* (2013.01); *A61M 16/0434* (2013.01); *A61M 16/0477* (2014.02); *A61M 16/0833* (2014.02); *A61M 16/1055* (2013.01); *A61M 16/208* (2013.01); *A61M 2016/003* (2013.01); *A61M 2016/0024* (2013.01); *A61M 2016/0027* (2013.01); *A61M 2202/0014* (2013.01); *A61M 2205/3334* (2013.01)

(56) References Cited

U.S. PATENT DOCUMENTS

| | | | |
|---|---|---|---|
| 5,419,769 A * | 5/1995 | Devlin | A61M 1/0039 604/118 |
| 5,492,109 A * | 2/1996 | Hirschl | A61M 1/32 128/201.21 |
| 6,516,803 B1 | 2/2003 | Enzinger | |
| 2002/0014238 A1* | 2/2002 | Kotmel | A61M 16/04 128/204.18 |
| 2003/0216698 A1* | 11/2003 | McNary | A61M 16/0463 604/264 |
| 2006/0207602 A1* | 9/2006 | Kolobow | A61M 16/0463 128/207.14 |
| 2008/0017198 A1* | 1/2008 | Ivri | A61M 11/005 128/204.21 |
| 2008/0021386 A1* | 1/2008 | Clayton | A61M 16/04 604/104 |
| 2008/0023005 A1* | 1/2008 | Tokunaga | A61M 16/0463 128/205.19 |
| 2008/0099025 A1* | 5/2008 | MacMillan | A61M 16/0479 128/207.15 |
| 2008/0257353 A1 | 10/2008 | Yamamoto et al. | |
| 2010/0229863 A1* | 9/2010 | Enk | A61M 16/0096 128/204.21 |
| 2011/0048427 A1* | 3/2011 | Zachar | A61L 29/085 128/207.15 |
| 2012/0024293 A1* | 2/2012 | Maguire | A61M 16/04 128/207.14 |
| 2012/0199127 A1* | 8/2012 | Garde | A61M 16/00 128/204.23 |

FOREIGN PATENT DOCUMENTS

| | | |
|---|---|---|
| JP | 2007-117273 A | 5/2007 |
| WO | WO-2006/009283 A2 | 1/2006 |
| WO | WO-2006/035769 A1 | 4/2006 |

* cited by examiner

SPUTUM ASPIRATING APPARATUS, ARTIFICIAL VENTILATION SYSTEM INCLUDING A SPUTUM ASPIRATING APPARATUS, AND METHOD FOR OPERATING A SPUTUM ASPIRATING APPARATUS

CROSS-REFERENCE TO RELATED APPLICATIONS

This application is the U.S. national stage application of International Patent Application No. PCT/JP2013/005478, filed Sep. 17, 2013, which claims priority to Japanese Application No. 2013-212886, filed Sep. 26, 2012, the disclosures of each of which are incorporated herein by reference in their entirety.

TECHNICAL FIELD

The present invention relates to a sputum apparatus, an artificial ventilation system, and a method for operating a sputum apparatus.

BACKGROUND ART

A patient using an artificial ventilator needs to undergo removal of sputum produced in the patient's trachea, by aspiration at periodic intervals. Such an operation for sputum is troublesome; this operation needs to be performed night and day; and nurses, caregivers, and others should bear a great burden of work.

In view of this, aspirating apparatuses that automatically perform the operation for sputum have been known. For example, sputum aspirating apparatuses for aspirating sputum of patients who have been artificially ventilated by tracheostomy are described in Patent Documents 1 and 2. These sputum aspirating apparatuses are configured to continuously produce negative pressure in order to aspirate sputum; and when the negative pressure of suction path becomes high, assume that the suction tube is blocked with sputum, and raise the negative pressure.

Patent Document 1: PCT International Publication No. WO2006/009283
Patent Document 2: Japanese Patent Application Laid-open No. 2007-117273

DISCLOSURE OF THE INVENTION

Problem to be Solved by the Invention

However, a suction cannula of the sputum aspirating apparatuses described in Patent Documents 1 and 2 was placed inside a tracheal cannula for air ventilation; and there was a risk of disturbing the ventilation, in cases where sputum which was not aspirated was accumulated inside the tracheal cannula. Further, there was a possibility of affecting the ventilation when the negative pressure was increased.

In view of the circumstances as described above, an object of the present invention is to provide a sputum apparatus capable of automatically aspirating sputum safely.

Means for Solving the Problem

In order to solve the problems described above, a sputum apparatus according to an embodiment of the present invention includes a suction line, a switching unit, a measurement unit, and a control unit.

The suction line has a suction inlet and an accommodating part. The suction inlet is capable of aspirating sputum produced in a patient's respiratory tract. The accommodating part accommodates the aspirated sputum and is maintained at a negative pressure.

The switching unit is capable of switching between a first state and a second state. The first state makes the suction inlet communicate with the accommodating part. The second state makes the suction inlet shut off from the accommodating part. The switching unit is placed in the suction line.

The measurement unit measures an expired air being aspirated into the accommodating part, under the first state.

The control unit is capable of switching the switching unit from the second state to the first state during expiration phase of the patient, and capable of keeping the switching unit to the first state when an amount of the expired air measured by the measurement unit is less than a predetermined value.

An artificial ventilation system according to an embodiment of the present invention includes an artificial ventilation unit, a suction line, a switching unit, a measurement unit, and a control unit.

The artificial ventilation unit ventilates a patient.

The suction line has an insertion part and an accommodating part. The insertion part includes a first passage and a second passage. The first passage is connectable to the artificial ventilation unit. The second passage is provided with a suction inlet to aspirate the patient's sputum. The insertion part is capable of being inserted into the patient's respiratory tract. The accommodating part accommodates the patient's sputum and is maintained at a negative pressure.

The switching unit is capable of switching between a first state and a second state. The first state makes the suction inlet communicate with the accommodating part. The second state makes the suction inlet shut off from the accommodating part. The switching unit is placed in the suction line.

The measurement unit measures an expired air being aspirated into the accommodating part, under the first state.

The control unit is capable of switching the switching unit from the second state to the first state during expiration phase of the patient, and capable of keeping the switching unit to the first state when an amount of the expired air measured by the measurement unit is less than a predetermined value.

A method according to an embodiment of the present invention is a method for operating a sputum apparatus including a suction line, a switching unit, a measurement unit, and a control unit. The suction line has a suction inlet to aspirate a patient's sputum and an accommodating part to accommodate the patient's sputum. The switching unit is placed in the suction line and is capable of switching between a first state and a second state. The first state makes the suction inlet communicate with the accommodating part. The second state makes the suction inlet shut off from the accommodating part. The measurement unit measures an expired air being aspirated into the accommodating part, under the first state.

The control unit switches the switching unit from the second state to the first state during expiration phase of the patient.

The control unit determines whether or not an amount of the expired air measured by the measurement unit is less than a predetermined value.

If the amount of the expired air is less than the predetermined value, the control unit keeps the switching unit to the first state.

MODE(S) FOR CARRYING OUT THE INVENTION

Figure 1:
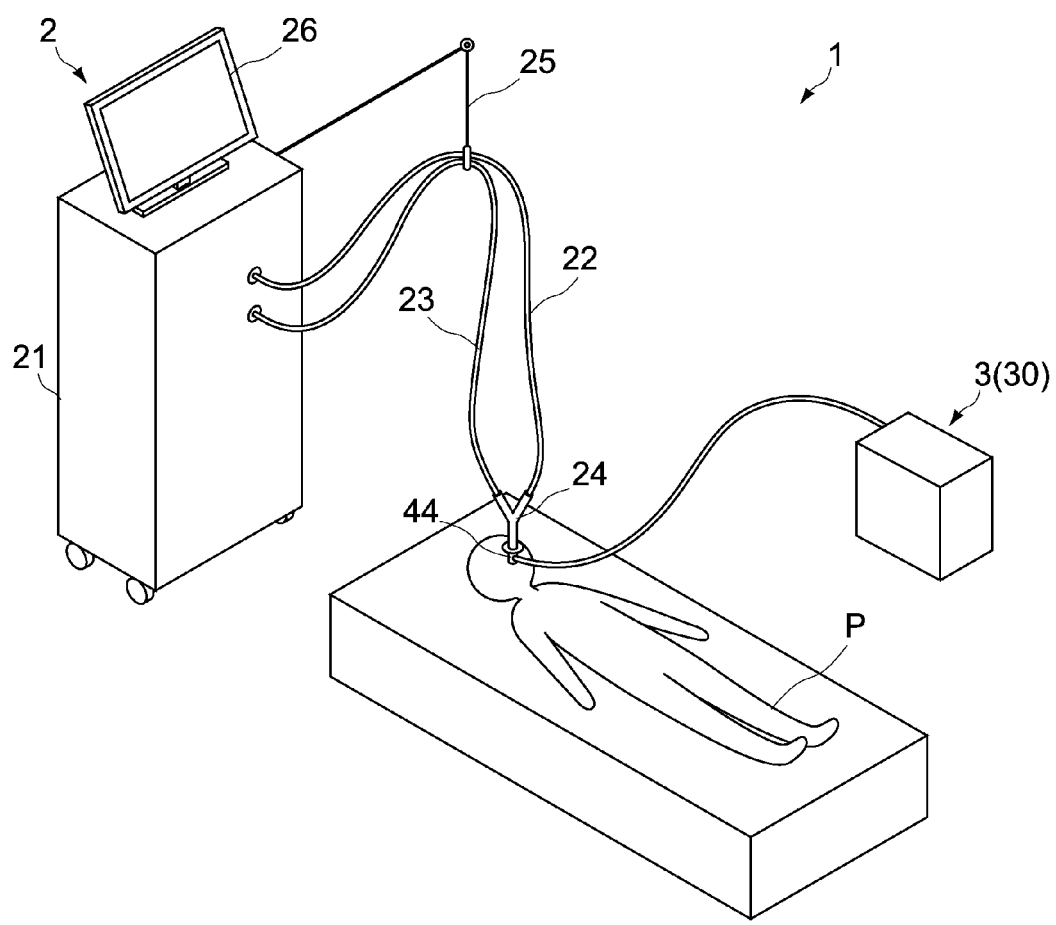
FIG. 1 A schematic diagram showing an artificial ventilation system according to a first embodiment of the present invention.

A sputum apparatus according to an embodiment of the present invention includes a suction line, a switching unit, a measurement unit, and a control unit.

The suction line has a suction inlet and an accommodating part. The suction inlet is capable of aspirating sputum produced in a patient's respiratory tract. The accommodating part accommodates the aspirated sputum and is maintained at a negative pressure.

The switching unit is capable of switching between a first state and a second state. The first state makes the suction inlet communicate with the accommodating part. The second state makes the suction inlet shut off from the accommodating part. The switching unit is placed in the suction line.

The measurement unit measures an expired air being aspirated into the accommodating part, under the first state.

The control unit is capable of switching the switching unit from the second state to the first state during expiration phase of the patient, and capable of keeping the switching unit to the first state when an amount of the expired air measured by the measurement unit is less than a predetermined value.

The sputum apparatus keeps the first state and aspirates the sputum, assuming that a place near the suction inlet is blocked with sputum, in cases where the amount of the expired air being aspirated under the first state is less than a predetermined value. It therefore enables to check whether the aspiration of the sputum is needed and to perform aspiration procedure, with the use of the expired air of the patient. This enables automatic aspiration of sputum, without affecting respiratory status of the patient. Further, it may allow the aspiration of sputum frequently, and thus allow the aspiration of sputum before the patient complains about discomfort. Thus, it makes it possible to perform the aspiration of sputum in a safe and automatic way.

The suction line may further have an insertion part which is capable of being inserted into the patient's respiratory tract.

The insertion part may include a first passage and a second passage. The first passage is connectable to an artificial ventilator. The second passage communicates with the suction inlet.

This allows the sputum apparatus to be connected to the artificial ventilator via the insertion part. It thus makes it possible to automatically aspirate sputum for a patient on a ventilator, and this may reduce the burden on the nurses and the like. Further, it makes it possible to perform aspiration procedure without disturbing the ventilation of the artificial ventilator.

The insertion part may have a tracheal tube, a balloon, and a third passage.

The tracheal tube has the first passage and the second passage being formed inside.

The balloon is provided on an outer periphery of the tracheal tube and is capable of being in close contact with the patient's respiratory tract.

The third passage is formed in the tracheal tube and is capable of sending air to the balloon.

The tracheal tube thus can have the configuration in which the first passage for ventilation by artificial breathing, the second passage for the aspirated sputum, and the third passage for balloon dilatation are integrally formed inside. It therefore can provide a configuration which allows the dilated balloon to more easily be in close contact with the outer periphery of the tracheal tube, and which is more resistant to leakage of ventilation gas from the artificial ventilator; compared to a configuration having a plurality of independent lines or the like. Further, as compared to a configuration having a plurality of independent lines or the like, it makes it possible to lessen risk of infection to the patient, reduce invasiveness, and improve safety.

The suction inlet may be opened in a radial direction of the tracheal tube.

The balloon may include a structured part forming a space facing the suction inlet.

With this configuration, the suction inlet may be in a form facing the respiratory tract; and this position makes it easier to aspirate the sputum accumulated on the inner walls of the trachea. In addition, the configuration with the structured part may facilitate the inflow of the sputum into the space facing the suction inlet. It therefore enables to perform aspiration in an efficient way, and to aspirate sputum safely while there is not so much sputum.

In addition, the sputum apparatus may further include a detection unit capable of detecting respiratory status of the patient.

The control unit may determine expiration phase of the patient, based on an output of the detection unit.

This may allow the control unit to appropriately switch the switching unit to the first state; based on the output of the detection unit equipped in the sputum apparatus itself.

Specifically, the detection unit may have a pressure sensor.

The insertion part may further have a fourth passage which is formed in the tracheal tube in such a manner that the fourth passage is communicated with the first passage.

The fourth passage may be connected to the pressure sensor.

This may allow the pressure sensor of the detection unit to measure an inner pressure of the first passage through the fourth passage. Therefore, the pressure sensor is able to measure the patient's airway pressure, and thus can detect the expiration phase of the patient. Further, it makes it possible to form the fourth passage integrally with an intubation tube.

Alternatively, the detection unit may have a sensor capable of detecting a flow direction of gas inside the tracheal tube.

This enables to appropriately keep track of the respiratory state of the patient also in cases where the patient is spontaneously breathing. It is therefore made possible to use this sputum apparatus during a treatment process from a serious ventilator-dependent condition until being freed from ventilator support.

The accommodating part may include a replaceable container which is connectable to a negative-pressure source.

This provides a sanitary way of disposing the container accommodating the sputum. Further, as it can eliminate the need of washing inside the container, it may reduce the burden on the nurses and the like.

The suction line may further have a deformable suction tube which is connected between the suction inlet and the accommodating part.

The switching unit may further have a clamp capable of opening and blocking the suction tube.

This enables opening and blocking the suction tube from the outside, which makes it possible to easily perform switching of the first and second states, with a simple configuration.

The control unit may keep the switching unit to the first state for a first period of time and determine whether or not the amount of the expired air being aspirated is less than the predetermined value.

If the amount of the expired air measured by the measurement unit is less than the predetermined value, the control unit may keep the switching unit to the first state for a second period of time longer than the first period of time.

With this configuration, the time for checking the necessity of aspiration of sputum can be made shorter than the time for aspirating the sputum. It therefore can shorten the time of being under the first state; which may reduce fluctuations in pressure in the accommodating part. It thus makes it possible to reduce power consumption of the negative-pressure source or the like for maintaining the pressure inside the accommodating part at the negative pressure.

An artificial ventilation system according to an embodiment of the present invention includes an artificial ventilation unit, a suction line, a switching unit, a measurement unit, and a control unit.

The artificial ventilation unit ventilates a patient.

The suction line has an insertion part and an accommodating part. The insertion part includes a first passage and a second passage. The first passage is connectable to the artificial ventilation unit. The second passage is provided with a suction inlet to aspirate the patient's sputum. The insertion part is capable of being inserted into the patient's respiratory tract. The accommodating part accommodates the patient's sputum and is maintained at a negative pressure.

The switching unit is capable of switching between a first state and a second state. The first state makes the suction inlet communicate with the accommodating part. The second state makes the suction inlet shut off from the accommodating part. The switching unit is placed in the suction line.

The measurement unit measures an expired air being aspirated into the accommodating part, under the first state.

The control unit is capable of switching the switching unit from the second state to the first state during expiration phase of the patient, and capable of keeping the switching unit to the first state when an amount of the expired air measured by the measurement unit is less than a predetermined value.

A method according to an embodiment of the present invention is a method for operating a sputum apparatus including a suction line, a switching unit, a measurement unit, and a control unit. The suction line has a suction inlet to aspirate a patient's sputum and an accommodating part to accommodate the patient's sputum. The switching unit is placed in the suction line and is capable of switching between a first state and a second state. The first state makes the suction inlet communicate with the accommodating part. The second state makes the suction inlet shut off from the accommodating part. The measurement unit measures an expired air being aspirated into the accommodating part, under the first state.

The control unit switches the switching unit from the second state to the first state during expiration phase of the patient.

The control unit determines whether or not an amount of the expired air measured by the measurement unit is less than a predetermined value.

If the amount of the expired air is less than the predetermined value, the control unit keeps the switching unit to the first state.

Hereinafter, some embodiments of the present invention will be described with reference to the drawings.

First Embodiment

Artificial Ventilation System

FIG. 1 is a schematic diagram showing an artificial ventilation system according to a first embodiment of the present invention. The artificial ventilation system 1 of this embodiment has an artificial ventilator 2 (artificial ventilation unit) and a sputum apparatus 3. The artificial ventilation system 1 is capable of performing an artificial respiration procedure with the artificial ventilator 2, for a patient P in a supine position. The configuration of the artificial ventilator 2 is not limited in particular, and the artificial ventilator 2 of this embodiment is applied to, for example, tracheal intubation. One example of the configuration of the artificial ventilator 2 will be described below.

The artificial ventilator 2 has a main body 21, an inspiratory circuit 22, an expiratory circuit 23, and a connecting part 24. The artificial ventilator 2 is configured to be capable of ventilating the patient P, by providing the patient P with an inspiratory gas having a predetermined oxygen level, from the main body 21 through the inspiratory circuit 22; and discharging an expired gas from the patient P, through the expiratory circuit 23.

The main body 21 may have a blower inside. The blower may, for example, take in some air and some oxygen from an oxygen source which is not shown, and send the oxygen gas having a predetermined concentration and a predetermined pressure, through an inspiratory valve or the like, toward the inspiratory circuit 22. Meanwhile, the expired gas discharged from the expiratory circuit 23 may be discharged to the atmosphere through an expiratory valve or the like.

Alternatively, the main body may further have a reservoir tank or the like. This makes it possible to store the oxygen in a pressurized state which has been pressurized by the blower, in the reservoir tank. It may thus enable to send the oxygen gas more smoothly.

The connecting part 24 has a tubular structure configured in a so-called Y-piece. That is, the connecting part 24 has one end which connects to an insertion part 44 to be inserted into the patient's respiratory tract; and another end branched in two to be connect to each of the inspiratory circuit 22 and the expiratory circuit 23. In a pipeline of the connecting part 24 connected to the inspiratory circuit 22, for example, a filter for prevention of infection may be placed.

In addition, the artificial ventilator 2 may have a holder 25 which ties the inspiratory circuit 22 and the expiratory circuit 23 and holds them at a predetermined position. Further, the artificial ventilator 2 may have a display 26 which connects to the main body 21. The display 26 may be made up of, for example, a touch panel or the like. The display 26 may be configured to be capable of displaying information such as respiratory status of the patient P; and letting input operation for selecting ventilation mode, or the like. Furthermore, the artificial ventilator 2 may also have an alarm device which notifies an abnormal state of the respiratory status of the patient P; a nebulizer for treating the respiratory tract of the patient P with humidification or the like; and other things as appropriate.

The patient P on the artificial ventilator 2 is not able to get sputum out of the respiratory tract on his or her own, so there was a risk that the sputum might be accumulated in the respiratory tract and disturb the ventilation of the artificial ventilator 2. Thus, there was a frequent need of sputum aspiration procedure; and it made nurses, caregivers, and others bear a great burden of work.

In view of this, the artificial ventilation system 1 has the sputum apparatus 3, and is configured to be capable of performing sputum aspiration procedure for the patient P who is seriously ill and unable to breathe spontaneously. Hereinafter, a configuration of the sputum apparatus 3 will be described.

[Sputum Apparatus]

Figure 2:
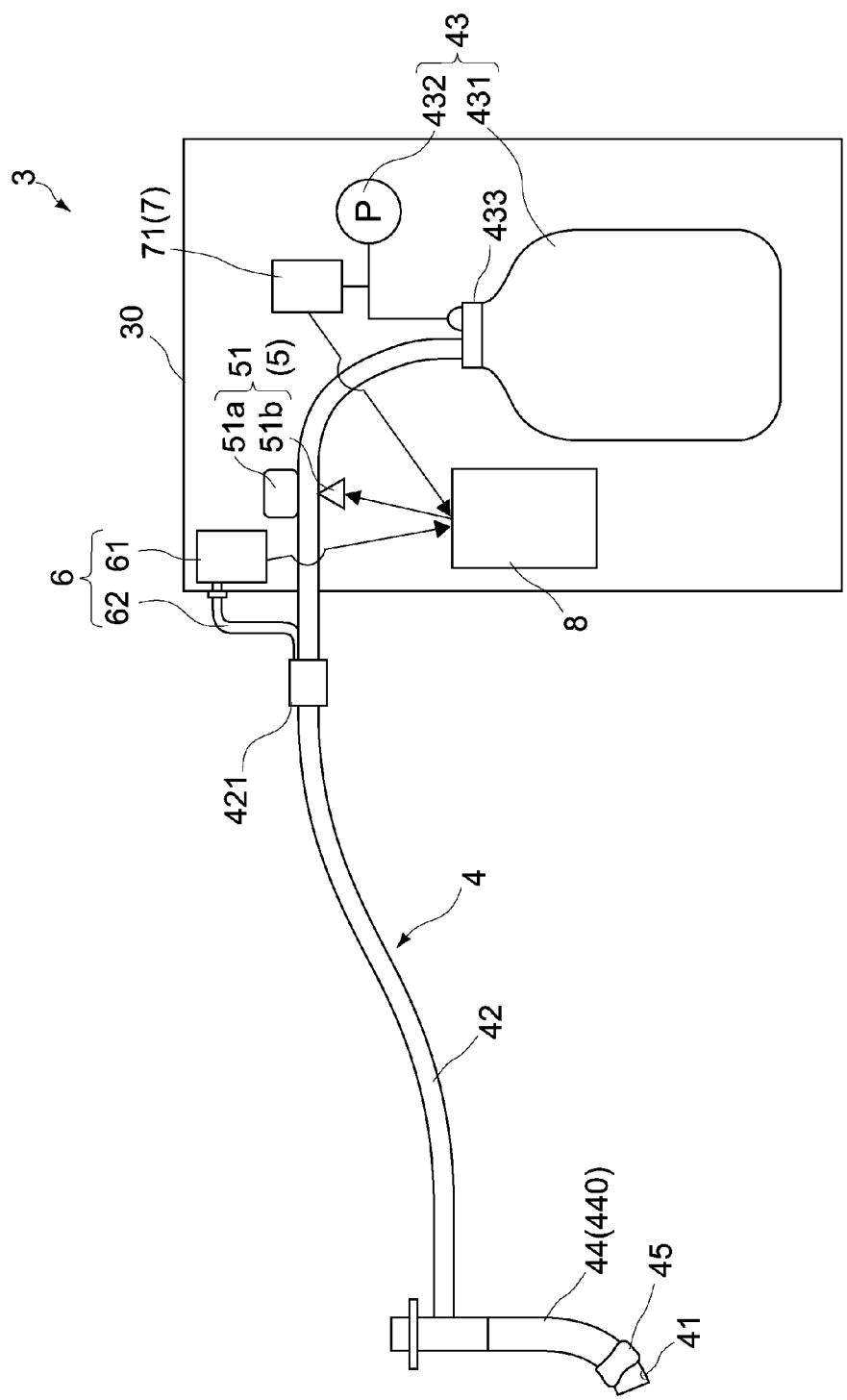
FIG. 2 A schematic diagram of a sputum apparatus shown in FIG. 1.
Figure 3:
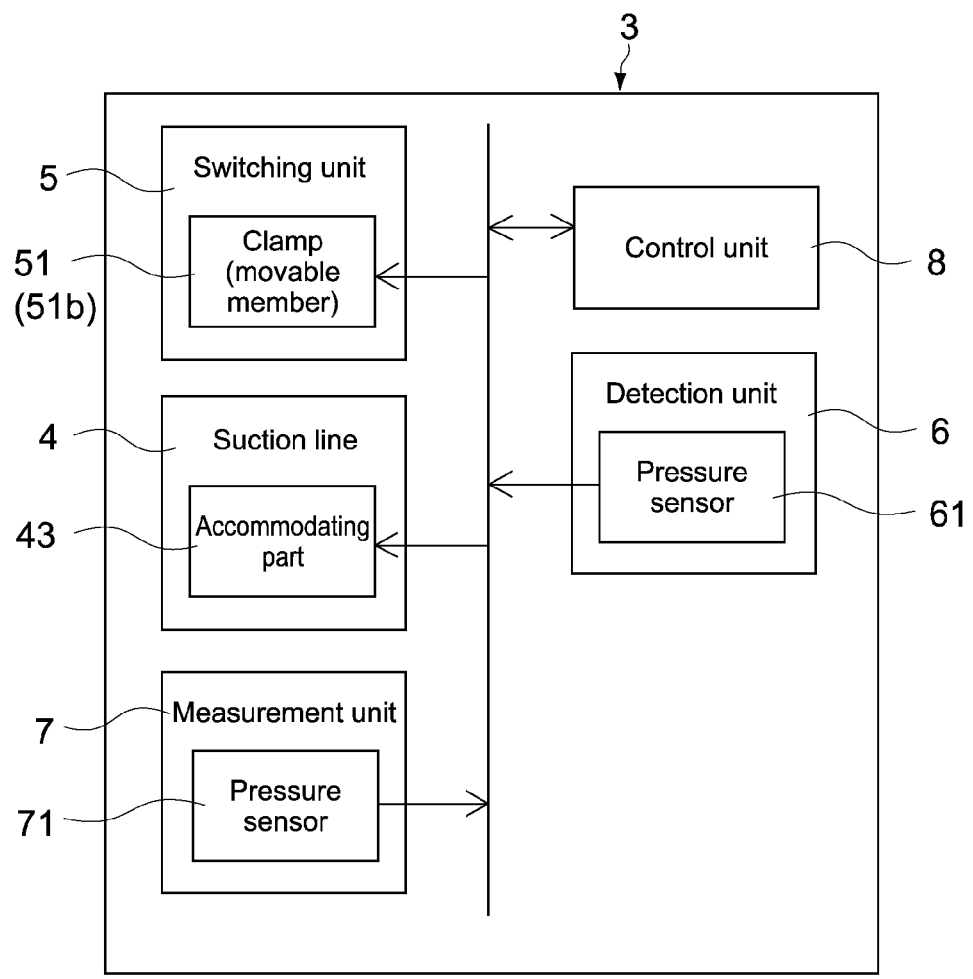
FIG. 3 A block diagram of an internal structure of the sputum apparatus shown in FIG. 1.

FIGS. 2 and 3 are diagrams showing the sputum apparatus 3 of this embodiment. FIG. 2 is a schematic diagram, and FIG. 3 is a block diagram showing an internal structure. The sputum apparatus 3 has a suction line 4, a switching unit 5, a detection unit 6, a measurement unit 7, and a control unit 8. The sputum apparatus 3 is configured in such a manner that the control unit 8 is able to control aspiration of sputum by the suction line 4. In addition, the switching unit 5, the measurement unit 7, the control unit 8, a portion of the suction line 4 and a portion of the detection unit 6 are placed inside a housing 30 of the sputum apparatus 3.

(Suction Line)

The suction line 4 has a suction inlet 41, a suction tube 42, an accommodating part 43 and an insertion part 44. Thus, the suction line 4 is capable of aspirating from the suction inlet 41 the sputum produced in the patient's respiratory tract; and is configured to aspirate the sputum from the suction tube 42 to the accommodating part 43.

As will be described later, the insertion part 44 has an intubation tube 440 (tracheal tube), which would be inserted into the patient's respiratory tract through the mouth. The suction inlet 41 opens toward an outer periphery of the intubation tube 440, and is placed in such a manner that the suction inlet 41 would face the patient's respiratory tract when the intubation tube 440 is inserted into the patient's respiratory tract.

The suction tube 42 is connected between the suction inlet 41 and the accommodating part 43, and is placed in such a manner that it penetrates the housing 30. In this embodiment, the suction tube 42 is configured to communicate with the suction inlet 41 by being connected to the insertion part 44. An inner part of the suction tube 42 forms a suction path (not shown). This suction path makes a passage for the sputum during aspiration of the sputum. That is, one end of the suction path would be connected to the suction inlet 41 via the intubation tube 440, and another end of the suction path would be connected to the accommodating part 43.

The suction tube 42 is deformable, and it is made of, for example, a polyurethane catheter tube or the like. The suction tube 42 may be a single lumen tube which forms the suction path alone, or may be formed as a double lumen tube. In cases where the suction tube 42 is formed as a double lumen tube, it is also possible that in addition to the suction path, an airway-pressure measurement path (not shown), which makes up a part of an airway-pressure measurement line 62 of the detection unit 6, may be formed. Such a suction tube 42 may include a branching part 421, for example, and may be configured in such a manner that the suction path and the airway-pressure measurement path run parallel to each other from the insertion part 44 to the branching part 421; and the suction path and the airway-pressure measurement path branch off from each other at the branching part 421. That is, in this case, the suction path alone would be placed between the branching part 421 and the accommodating part 43. It should be noted that the branching part 421 may be placed outside the housing 30 as shown in FIG. 2, or may be placed inside the housing 30.

Further, the suction tube 42 may be configured to be replaceable. That is, it may be configured in such a way that the used suction tube 42 can be detached from the intubation tube 440 and the accommodating part 43; and a new suction tube 42 can be connected to the intubation tube 440 and the accommodating part 43. With this configuration, it is possible to replace the suction tube 42 as may be necessary, and allows a procedure for sputum to be performed in a more sanitary way.

The accommodating part 43 has a container 431 and a negative-pressure source 432.

The container 431 accommodates the sputum being aspirated through the suction tube 42. The container 431 is maintained at a negative pressure. In this embodiment, the container 431 includes a cap portion 433 which is connected to the suction tube 42 and the negative-pressure source 432. The negative-pressure source 432 is made up of, for example, a diaphragm vacuum pump or the like, whose air-intake inlet is made to connect to the container 431. This enables to maintain a predetermined negative pressure inside the container 431. The predetermined negative pressure is not limited in particular, and for example, it may be about −400 mmHg (about −53.3 kPa, gauge pressure). It should be noted that the configuration of the negative-pressure source 432 is not limited to the above, and it is also possible to employ other vacuum pumps or the like.

The container 431 in this embodiment is configured to be replaceable. With this configuration, since it is possible to replace the container 431 when more than a predetermined volume of sputum is accommodated in the container 431, it may prevent infection, and enable disposal in a more sanitary way. Further, as it can eliminate the need of washing inside the container 431, it may reduce the burden on the nurses and the like.

The container 431 may be made up of, for example, a flexible soft bag. Examples of the soft bags that can be used include those made of a synthetic resin such as polypropylene resin, polyethylene resin and nylon resin. This makes it possible to produce the container 431 more inexpensively than producing a container made of glass or the like; which may reduce the cost of replacement. Moreover, at the time of replacement, it is possible to discard the container 431 after evacuating the air inside by pressing the container 431 from the outside, or the like. This may contribute to reduction of waste.

Figure 4:
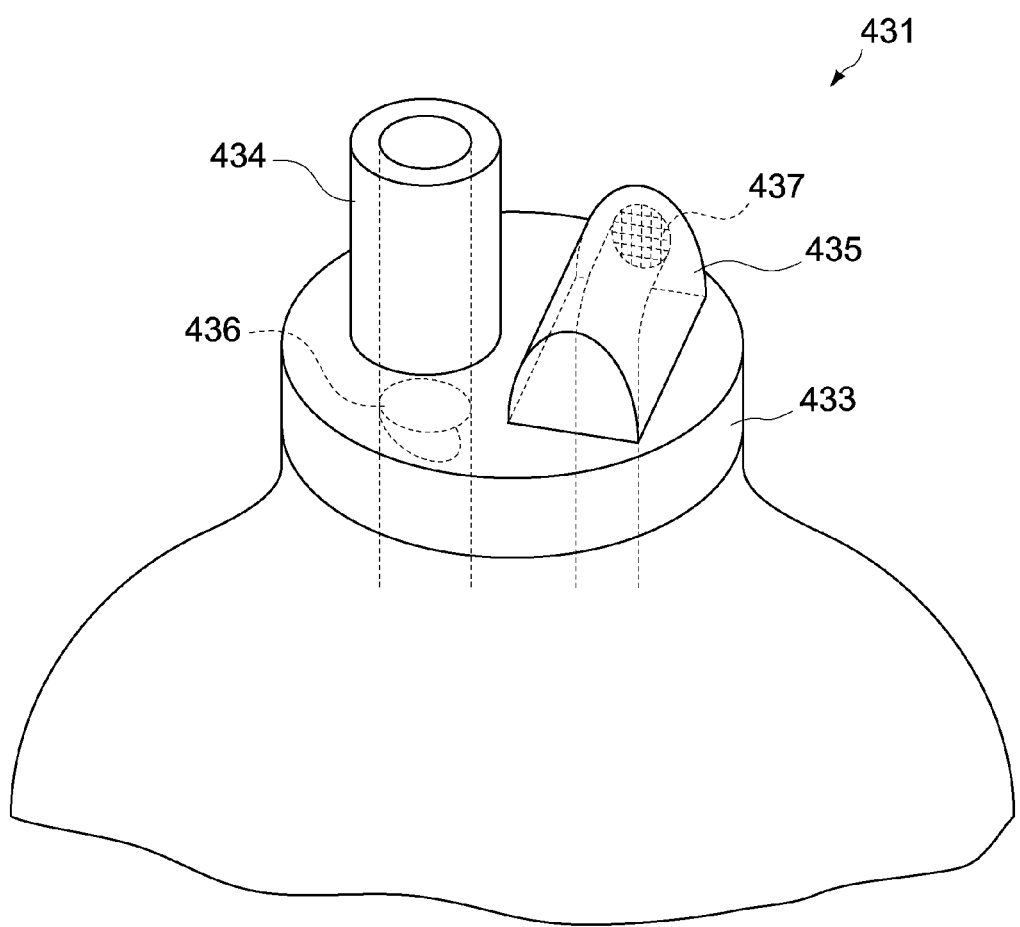
FIG. 4 A diagram of main component of a container shown in FIG. 2.

FIG. 4 is a schematic diagram showing the cap portion 433 of the container 431 of this embodiment. The cap portion 433 has a sputum removal port 434 to be connected to the suction tube 42; and an air-intake port 435 to be connected to the air-intake inlet of the negative-pressure source 432.

The sputum removal port 434 is provided with, for example, a check valve 436. The check valve 436 is configured to permit the flow of the sputum from the suction tube 42 to the container 431, and prevent the backward flow from the container 431 to the suction tube 42. The configuration of the check valve 436 is not limited in particular, and for example, a swing check valve may be employed.

The check valve 436 may be configured to be opened when a pressure is applied from the suction tube 42 into the container 431. For example, during the operation of the sputum apparatus 3, the suction inlet 41 is at about atmospheric pressure while an inner pressure of the container 431 is maintained at a negative pressure. As a result, a pressure may be applied from the suction tube 42 into the container 431, and thus the check valve 436 may be opened. On the other hand, at the time of disposal, the connection between the container 431 and the negative-pressure source 432 may be cancelled; and further, a pressure may be applied from the inside of the container 431 to the outside, by a process such as pressing the container 431 for evacuating the air. As a result, the check valve 436 may be closed; and it may prevent the air from flowing back into the container 431. It should be noted that a valve-opening pressure of the check valve 436 may be appropriately set to enable the above-mentioned open and close operation.

The air-intake port 435 is provided with, for example, a filter 437. Examples of filters that can be employed as the filter 437 include those such as a membrane filter having a pore diameter of about 0.45 to 0.8 μm, which may be made of cellulose acetate or the like. Such a filter 437 may be configured to be capable of, for example, allowing air to pass through if there is no deposition of liquid, and shutting off the air passage if a liquid is deposited on the filter 437. With this configuration, the negative-pressure source 432 is able to intake the air inside the container 431 through the filter 437, during the operation of the sputum apparatus 3. On the other hand, at the time of disposal, it becomes possible to evacuate the air inside the container 431 through the filter 437, by a process such as pressing the container 431. Further, if the air inside the container 431 is evacuated and if there is sputum deposited on the filter 437, the air passage would be shut off, and therefore it becomes possible to prevent the air from flowing back into the container 431; which allows the container 431 to remain in a state where the volume is reduced, after the evacuation of the air.

(Switching Unit)

The switching unit 5 is configured to be capable of switching between a first state and a second state. The first state makes the suction inlet 41 communicate with the accommodating part 43. The second state makes the suction inlet 41 shut off from the accommodating part 43. In this embodiment, the switching unit 5 has a clamp 51 which is capable of opening and blocking the suction tube 42.

The clamp 51 has, for example, a fixed member 51a and a movable member 51b which are placed across the suction tube 42. In the first state, the fixed member 51a and the movable member 51b are placed opposite each other in such a manner that a tubular shape of the suction tube 42 can be maintained; and the suction path in the suction tube 42 is opened. On the other hand, in the second state, by a shift of the movable member 51b toward the fixed member 51a, the suction tube 42 is deformed as if squeezed in a radial direction. This allows the opposed inner surfaces of the suction tube 42 to contact each other, to close the suction path.

In addition, for example, it is possible to use a solenoid for driving the movable member 51b. This enables to promptly switch the first and second states, based on an output of the control unit 8. Note that it is also possible to use other actuators such as a cylinder, for driving the movable member 51b.

Besides, in cases where the airway-pressure measurement path is formed in the suction tube 42, the clamp 51 may be placed between the branching part 421 and the accommodating part 43. This allows the suction path alone to be opened and closed by the clamp 51, while keeping the airway-pressure measurement path open at all times. Note that the suction path between the clamp 51 and the container 431 would be maintained at the negative pressure similar to that of the inside of the container 431, under the second state.

(Detection Unit)

In this embodiment, the detection unit 6 has a pressure sensor 61 and the airway-pressure measurement line 62; and detects the respiratory status of the patient by measuring the airway pressure. The airway-pressure measurement line 62 is a passage to connect the insertion part 44 and the pressure sensor 61; and is configured to communicate with the respiratory tract. In addition, as mentioned above, a part of the airway-pressure measurement line 62 may be made up of the airway-pressure measurement path which is formed inside the suction tube 42. In this case, the airway-pressure measurement line 62 may be configured to branch off from the suction path at the branching part 421 and connect to the pressure sensor 61 in the housing 30.

The pressure sensor 61 may be placed inside the housing 30, for example. The pressure sensor 61 measures the airway pressure through the airway-pressure measurement line 62. The configuration of the pressure sensor 61 is not limited in particular, and for example, may be made up of a diaphragm gauge, or the like.

Figure 5:
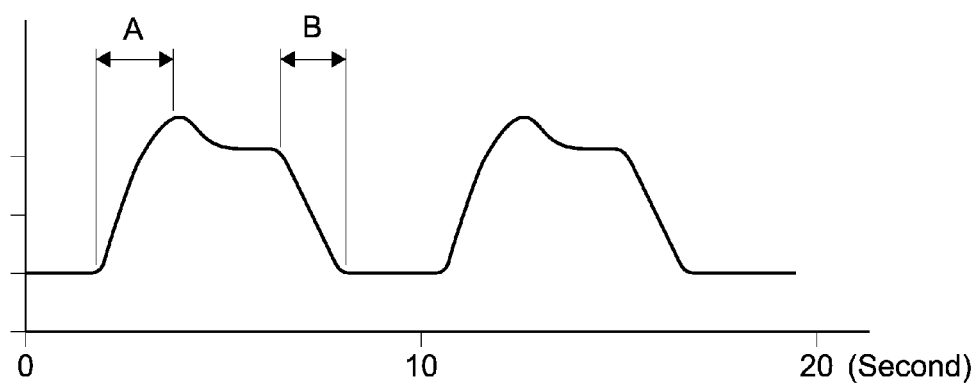
FIG. 5 A graph of a typical example of the changes in airway pressure, measured by a pressure sensor of a detection unit shown in FIG. 3, in which the ordinate indicates a value of the airway pressure; and the abscissa indicates time.

FIG. 5 is a graph showing a typical example of the changes in the airway pressure measured by the pressure sensor 61. The ordinate indicates a value of the airway pressure; and the abscissa indicates time. For example, in a period of time indicated by "A" of FIG. 5, the airway pressure is increased. This indicates an inspiratory phase. Meanwhile, in a period of time indicated by "B" of FIG. 5, the airway pressure is decreased. This indicates an expiration phase. It is thus possible to detect the respiratory status by measuring the airway pressure.

(Measurement Unit)

The measurement unit 7 measures an expired air being aspirated into the accommodating part 43, under the first state. With this configuration, the measurement unit 7 is configured to monitor the status of production of sputum in the respiratory tract.

For example, under the first state, since the accommodating part 43 maintained at the negative pressure is communicated with the suction inlet 41 opened toward the respiratory tract, the expired air would be aspirated into the accommodating part 43 unless the suction inlet 41 is blocked with sputum. However, in cases where the suction inlet 41 is blocked with sputum, an amount of the expired air being aspirated into the accommodating part 43 would decrease, or almost no air would be aspirated. In this way, the measurement unit 7 is able to monitor the status of production of sputum in the respiratory tract, by measuring the amount of the expired air aspirated into the accommodating part 43, under the first state.

The measurement unit 7 has a pressure sensor 71 placed at the accommodating part 43. The pressure sensor 71 is placed in such a manner that it would be able to measure the pressure inside the container 431. For example, the pressure sensor 71 may be placed between the container 431 and the negative-pressure source 432, where the pressure is maintained at the negative pressure similar to that of the inside of the container 431. It is therefore made possible to detect the amount of the expired air aspirated into the accommodating part 43, under the first state where the suction inlet 41 and the container 431 are open to each other, since the pressure inside the container 431 changes depending on the amount of the expired air being aspirated. The configuration of the pressure sensor 71 is not limited in particular, and for example, may be made up of a diaphragm gauge, or the like.

Note that the pressure sensor 71 may be capable of monitoring the pressure inside the container 431 under the second state as well. This makes it possible to maintain the pressure inside the container 431 at a pressure lower than a predetermined value, by activating the negative-pressure source 432 in cases where the aspiration or the like raises the pressure inside the container 431 to the pressure equal to or higher than the predetermined value. Thus, the sputum apparatus 3 of this embodiment is able to monitor the status of production of sputum and monitor the pressure inside the container 431 by one pressure sensor 71. This makes it possible to reduce the cost and complexity of the apparatus.

(Control Unit)

The control unit 8 is typically made up of CPU (Central Processing Unit) or MPU (Micro-Processing Unit). The control unit 8 executes a program stored in a memory (not shown), and the like, to execute a predetermined process.

The control unit 8 is capable of switching the switching unit 5 from the second state to the first state during expiration phase of the patient, and capable of keeping the switching unit 5 to the first state when the amount of the expired air measured by the measurement unit 7 is less than the predetermined value.

Figure 6:
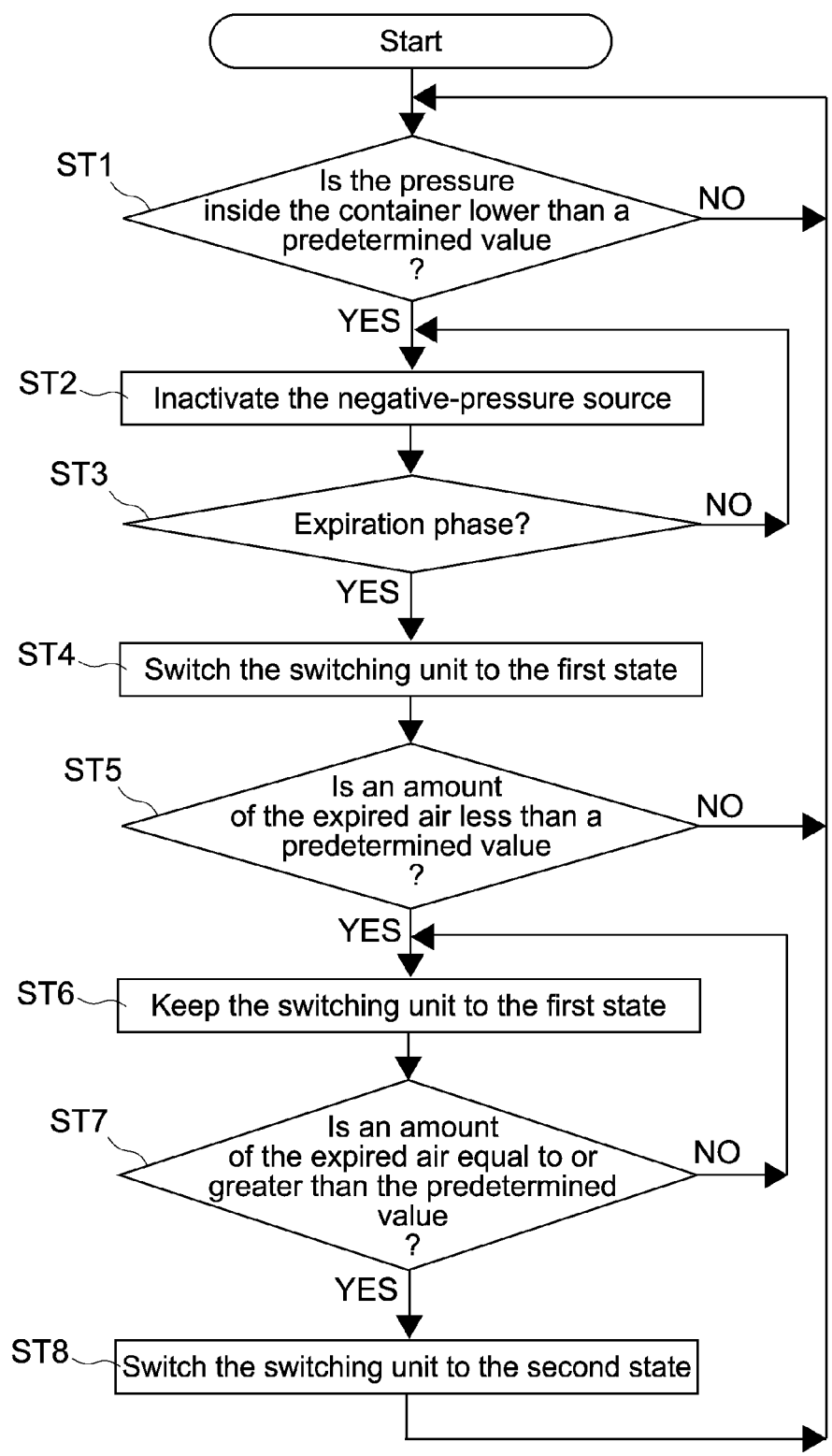
FIG. 6 A flowchart describing an operation of a control unit (sputum apparatus) shown in FIG. 3.

FIG. 6 is a flowchart describing an operation of the control unit 8 (sputum apparatus 3). The operation of the control unit 8 will be described below with reference to FIG. 6.

First, the sputum apparatus 3 is started up and the negative-pressure source 432 is activated. At this time, the switching unit 5 is under the second state where the suction tube 42 is closed by the clamp 51; and the communication of air between the suction inlet 41 and the accommodating part 43 is blocked.

The control unit 8 determines whether or not the pressure inside the container 431 is lower than a predetermined value, based on an output of the pressure sensor 71 of the measurement unit 7 (Step ST1). In this embodiment, the "predetermined value" of the pressure inside the container 431 may be, for example, −400 mmHg (about −53.3 kPa, gauge pressure). If it is determined that the pressure inside the container 431 is equal to or higher than the predetermined value (Step ST1, No), the control unit 8 keeps on activating the negative-pressure source 432 and performs the determination again in the same way (Step ST1).

If it is determined that the pressure inside the container 431 is lower than the predetermined value (Step ST1, Yes), the control unit 8 temporarily inactivates the negative-pressure source 432 (Step ST2). Since the switching unit 5 is in the second state, at this time, even when the negative-pressure source 432 is inactivated, the pressure inside the container 431 would be maintained at, for example, a pressure lower than the predetermined value.

Next, the control unit 8 determines whether or not it is in the expiration phase, based on an output of the pressure sensor 61 of the detection unit 6 (Step ST3). That is, it determines whether or not the airway pressure measured by the pressure sensor 61 is decreased. If the airway pressure measured by the pressure sensor 61 is not decreased, and it is determined that it is not in the expiration phase (Step ST3, No), the control unit 8 determines whether or not it is in the expiration phase, again (Step ST3).

If it is determined that it is in the expiration phase (Step ST3, Yes); the control unit 8 opens the suction tube 42 with the clamp 51, and switches the switching unit 5 to the first state (Step ET4). This allows the container 431 to communicate with the suction inlet 41. The control unit 8 keeps the switching unit 5 to the first state for a first period of time.

Then, the control unit 8 switches the state to the second state after the elapse of the first period of time. The control unit 8 then determines whether or not an amount of the expired air being aspirated into the accommodating part 43 is less than a predetermined value (Step ST5). That is, it determines whether or not the pressure inside the container 431 is lower than the predetermined value, based on an output of the pressure sensor 71 of the measurement unit 7.

For example, in cases where there is not so much production of sputum to block the suction inlet 41, the respiratory tract of the patient is kept in communication with the accommodating part 43 via the suction inlet 41; and the expired air of the patient would be aspirated into the accommodating part 43. However, in cases where the suction inlet 41 is blocked with sputum, the respiratory tract of the patient and the accommodating part 43 would be shut off from each other even under the first state; and thus the expired air of the patient would not be aspirated. Consequently, it is possible to check whether the aspiration of the sputum is needed, by measuring the amount of the expired air being aspirated into the accommodating part 43, that is, the pressure inside the container 431.

In addition, the first period of time may be a period of time where it would be possible to observe the aspiration of the expired air when the respiratory tract of the patient is kept in communication with the accommodating part 43 via the suction inlet 41, the expired air being aspirated into the container 431. In this embodiment, the first period of time may be a period of time where an increase in the pressure inside the container 431 due to the aspiration of the expired air can be measured. For example, the first period of time may be from 0.1 to 3.0 seconds. Further, after the elapse of the first period of time, the switching unit 5 is switched to the second state. Thus, by shortening the time for which the suction line 4 is open, it would be possible to restrict the increase in the pressure inside the container 431 and shorten the driving time of the negative-pressure source 432. This makes it possible to reduce power consumption, and the like.

If the pressure measured by the pressure sensor 71 is equal to or higher than the predetermined value (Step ST5, No), the control unit 8 determines that the production of sputum is not so much and it does not need to aspirate the sputum. Thus, in this case, it does not perform the aspiration of sputum; and it would determine whether or not the pressure inside the container 431 is lower than the predetermined value, again (Step ST1).

If it is determined that the pressure measured by the pressure sensor 71 is lower than the predetermined value, (Step ST4, Yes); there is a possibility that the suction inlet 41 has been blocked with sputum. Thus, the control unit 8 switches the switching unit 5 to the first state, keeps the first state, and aspirates the sputum blocking the suction inlet 41 (Step ST6).

Now, while the pressure of the suction inlet 41 is almost equal to the atmospheric pressure, the pressure inside the container 431 of the accommodating part 43 is a negative pressure at a value lower than the predetermined value. As a result, when the suction inlet 41 and the accommodating part 43 become open to each other, a pressure difference would be produced in the suction line 4. Therefore, with the switching unit 5 being kept to the first state, it enables to aspirate the sputum quickly from the suction inlet 41 via the suction tube 42 into the accommodating part 43.

While keeping the first state, the control unit 8 determines whether or not the pressure inside the container 431 is equal to or higher than the predetermined value, that is, whether or not an amount of the expired air is equal to or greater than a predetermined value (Step ST7). This makes it possible to check whether or not the sputum blocking the suction inlet 41 has been successfully removed. During the state where it is determined that the pressure inside the container 431 is lower than the predetermined value (Step ST7, No), there is a possibility that the suction inlet 41 is still blocked with sputum, so it would keep the switching unit 5 to the first state and continues with the aspiration (Step ST6).

If it is determined that the pressure inside the container 431 is equal to or higher than the predetermined value (Step ST7, Yes), it can be assumed that the sputum which has been blocking the suction inlet 41 is removed and thus the expired air is aspirated into the container 431. Therefore, the switching unit 5 would be switched to the second state (Step ST8). In this way, the control unit 8 keeps the first state until the sputum that blocks the suction inlet 41 is aspirated; and allows the suction line 4 to continue with the aspiration. Consequently, the control unit 8 keeps the switching unit 5 to the first state for a second period of time, which is longer than the first period of time. The second period of time may depend on the status of production of sputum, and may be from 0.3 to 3.0 seconds.

After finishing the aspiration, in order to maintain the pressure inside the container 431 to the pressure lower than the predetermined value, it would be determined whether or not the pressure inside the container 431 is lower than the predetermined value, again (Step ST1).

As described above, the control unit 8 of this embodiment may check whether the aspiration of the sputum is needed, during expiration phase; and it may aspirate the sputum quickly when it determines that the aspiration is needed. It thus makes it possible to automatically perform the aspiration as needed; and this may greatly reduce the burden on the nurses and the like. Further, since it makes it possible to check the need of the aspiration frequently, it may avoid the situation that a lot of sputum arises; and this may reduce the risk of disturbing the ventilation of the artificial ventilator 2.

In addition, by performing the aspiration during expiration phase, it may allow the ventilation and aspiration as if coughing, for example.

Moreover, with this embodiment, since it is possible to avoid the situation that a lot of sputum arises, and may make the volume of aspiration small; the time for performing the aspiration may be from 0.3 to 3.0 seconds. That is, as the expiration phase is supposed to be about 2 to 3 seconds, it is very unlikely that the aspiration lasts until the inspiratory phase of the patient. By performing the aspiration during expiration phase in such a way, it is possible to perform the aspiration without disturbing the ventilation, in the same way as, for example, coughing. Therefore, the sputum apparatus 3 is able to perform the aspiration safely.

Further, after the aspiration of the sputum, the control unit 8 makes the suction inlet 41 shut off from the accommodating part 43, and this prevents the increase in the pressure inside the container 431 of the accommodating part 43. In addition, the control unit 8 may monitor the output result of the measurement unit 7, after checking the need of the aspiration, and after aspirating the sputum; and may activate the negative-pressure source 432 only in cases where the pressure inside the container 431 is increased. Thus, in this embodiment, the negative-pressure source 432 is activated only in cases where it is necessary. It is therefore made possible to reduce power consumption for the activation of the negative-pressure source 432; and also to reduce the patient's burden by ensuring quietness.

Now, as mentioned above, the sputum apparatus 3 is able to be connected to the artificial ventilator 2 by the insertion part 44. The configuration of the insertion part 44 will be described below.

(Insertion Part)

Figure 7:
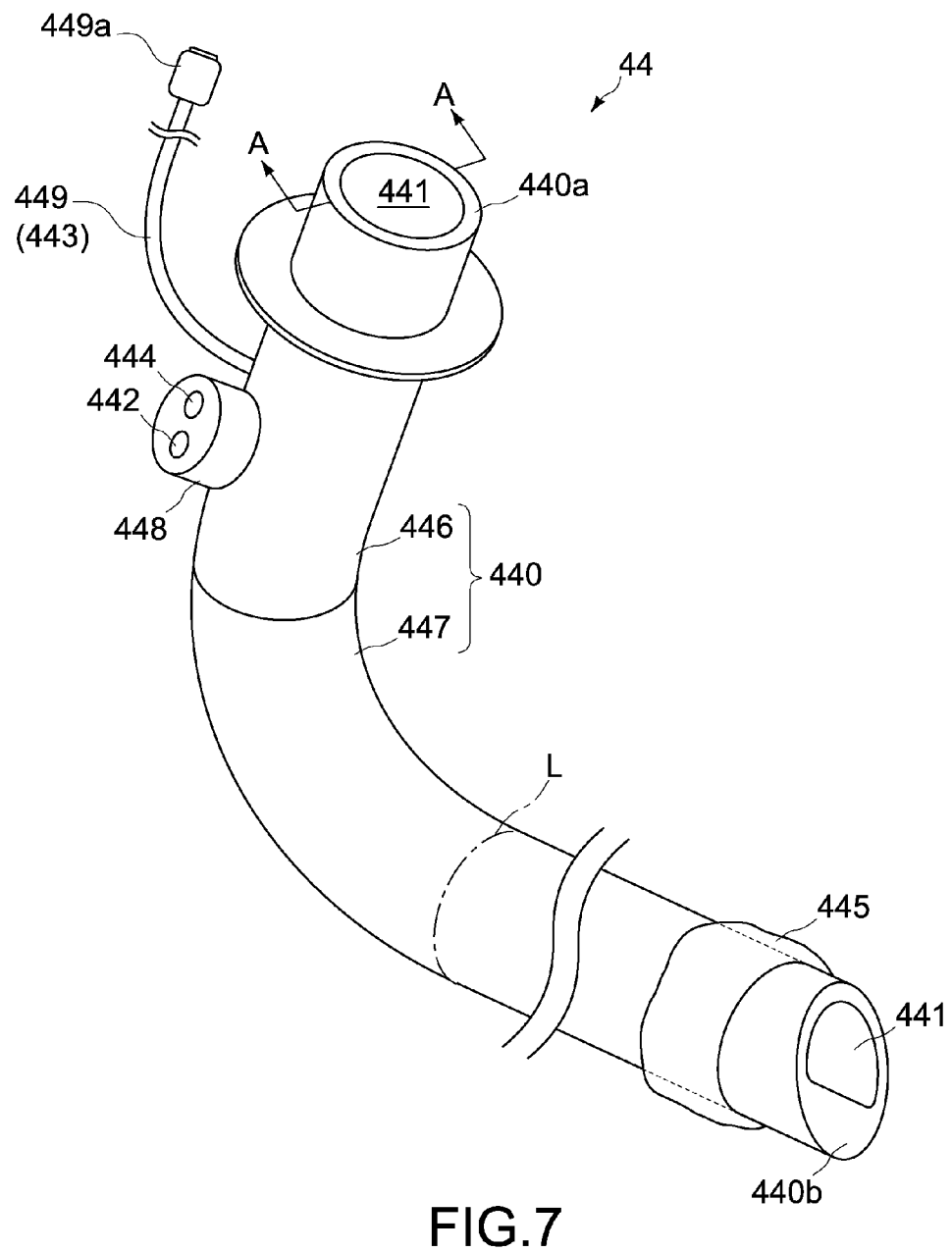
FIG. 7 A perspective view of an insertion part shown in FIG. 2.

FIG. 7 is a perspective view showing the configuration of the insertion part 44. The insertion part 44 has the intubation tube 440, a first passage 441, a second passage 442, a third passage 443, a fourth passage 444 and a balloon 445. The first passage 441 is connected to the artificial ventilator 2, to make up a passage for the expired air and inspiratory air for the patient. The second passage 442 makes up a passage for the sputum during the aspiration. The third passage 443 makes up a passage to send air to the balloon 445. The fourth passage 444 would be connected to the airway-pressure measurement line 62 of the detection unit 6.

The intubation tube 440 further has a connecting part 446 to be connected to the artificial ventilator 2 and the suction tube 42; and a tube body 447 to be inserted into the patient's respiratory tract. The connecting part 446 and the tube body 447 are connected with each other; and thus the intubation tube 440 is made in a curved tubular shape as a whole. That is, the connecting part 446 includes a first end 440a; and the tube body 447 includes a second end 440b.

Figure 8:
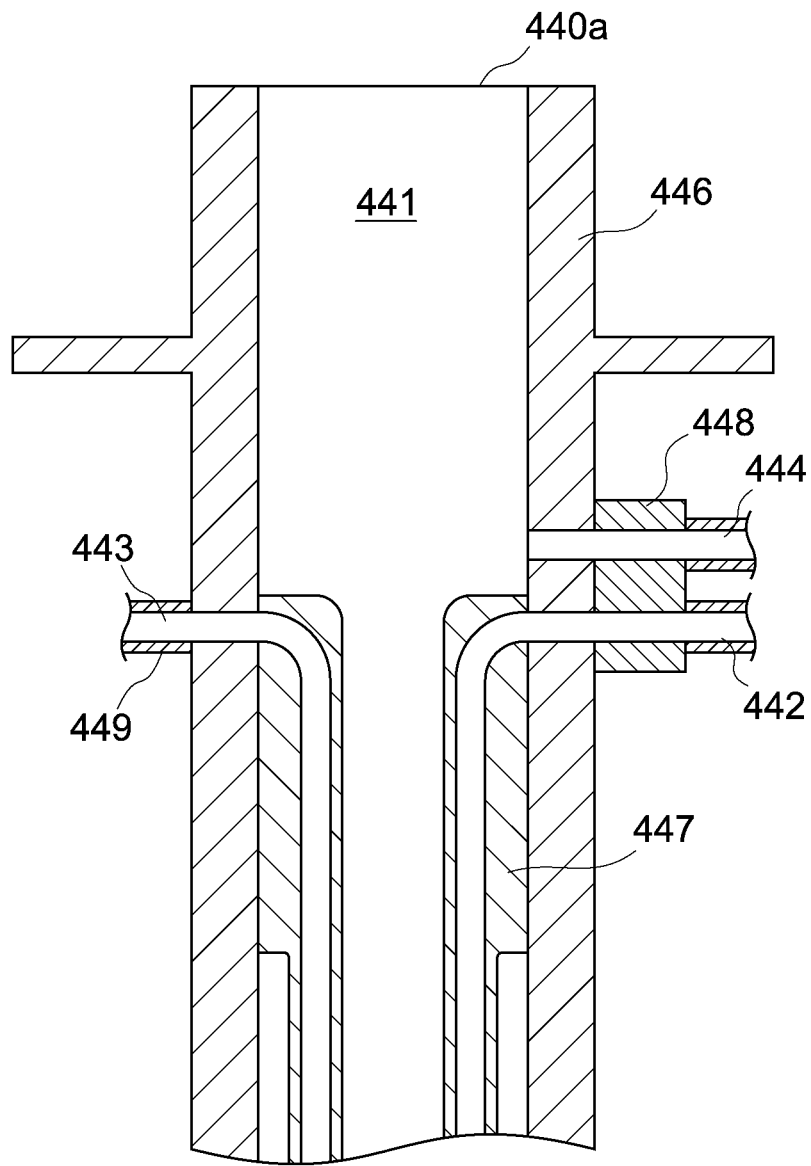
FIG. 8 A cross-sectional view taken along the line A-A in FIG. 7.

FIG. 8 is a cross-sectional view showing the configuration including the first end 440a of the connecting part 446; and this is a cross-sectional view taken along the line A-A in FIG. 7. The connecting part 446 includes a suction-tube connection 448 and a balloon-dilatation port 449. The suction-tube connection 448 and the balloon-dilatation port 449 are placed at an outer periphery of the connecting part 446. As shown in FIG. 8, one end of the tube body 447 is fit into the connecting part 446.

The suction-tube connection 448 would be connected to the suction tube 42. The second passage 442 and the fourth passage 444 are formed inside the suction-tube connection 448. The second passage 442 would be connected to the suction path of the suction tube 42; and from the suction-tube connection 448, the second passage 42 would be formed through the tube body 447 up to the suction inlet 41. The fourth passage 444 would be connected to the airway-pressure measurement path of the suction tube 42; and opens toward the first passage 441 from the suction-tube connection 448.

The third passage 443 is formed inside the balloon-dilatation port 449. The balloon-dilatation port 449 includes a valve 449a, which is placed at its end for insertion of a syringe barrel and injection of air (see FIG. 7). In addition, the third passage 443 would be connected to a delivery outlet 443a of the balloon 445, which will be described later; and from the delivery outlet 443a, the third passage 443 would be continuously formed through the tube body 447 up to the balloon-dilatation port 449.

The first passage 441 is formed inside the connecting part 446 and the tube body 447. The first passage 441 is formed to penetrate through the first and second ends 440a and 440b. Therefore, the first passage 441 is connectable to the artificial ventilator 2 through the connecting part 446, to be communicated with the respiratory tract of the patient. This makes the pressure inside the first passage 441 become the same as the airway pressure.

The fourth passage 444 would be connected to the pressure sensor 61, through the airway-pressure measurement line 62. This allows the pressure sensor 61 to measure the airway pressure through the airway-pressure measurement line 62 and the fourth passage 444.

With this configuration, the pressure sensor 61 does not have to be placed inside the intubation tube 440; and it makes it possible to keep the fourth passage 444 open. It is therefore made possible to simplify the configuration of the apparatus, and it is advantageous in view of costs.

Figure 9:
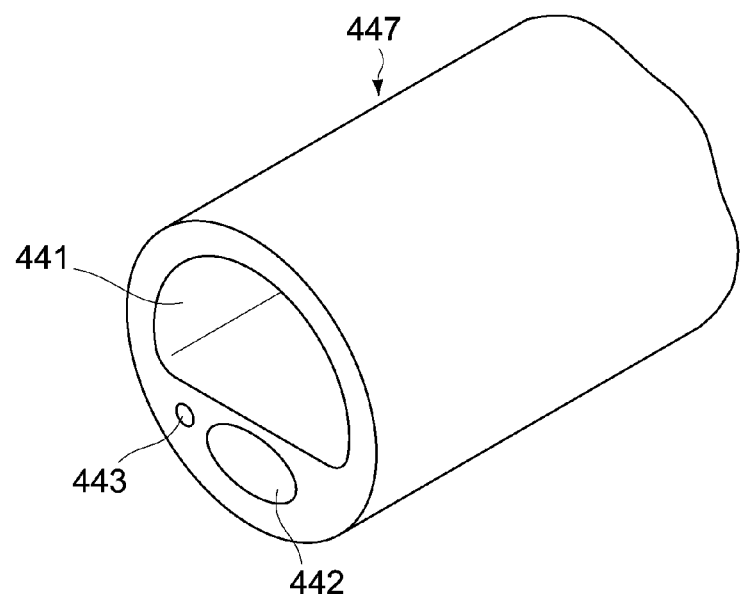
FIG. 9 A perspective view of main component of an intubation tube shown in FIG. 7, shown in a form cut with "L" in FIG. 7, for explanation.

FIG. 9 is a perspective view of the tube body 447, shown in a form cut with "L" in FIG. 7, for explanation. In this way, the tube body 447 has the first passage 441, the second passage 442 and the third passage 443 formed in parallel. Note that the tube body 447 having this shape may be easily formed by extrusion molding or the like.

Figure 10:
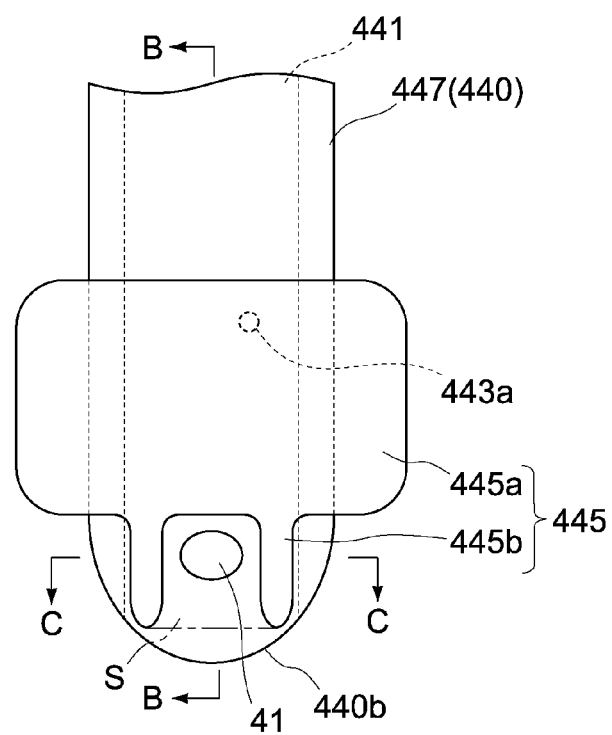
FIG. 10 A plan view of the intubation tube and a balloon shown in FIG. 7.
Figure 11:
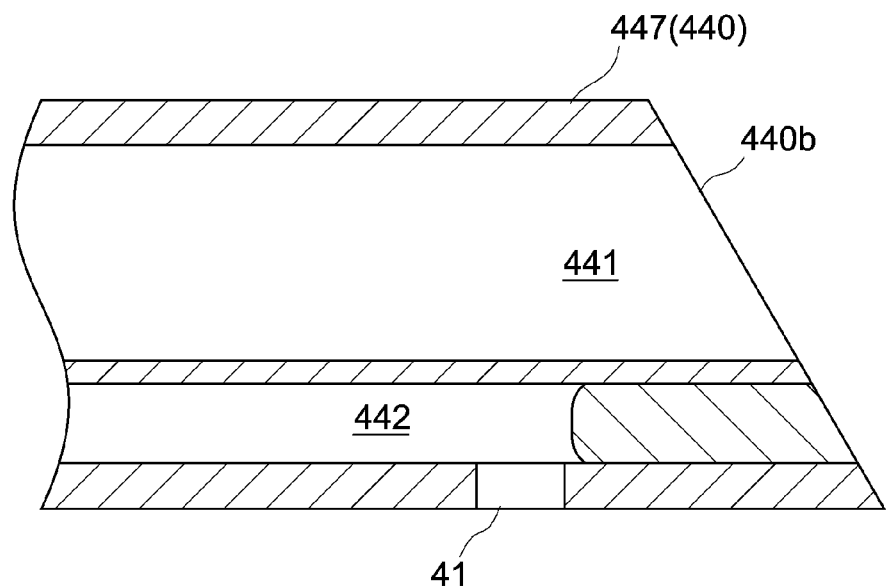
FIG. 11 A cross-sectional view taken along the line B-B in FIG. 10.
Figure 12:
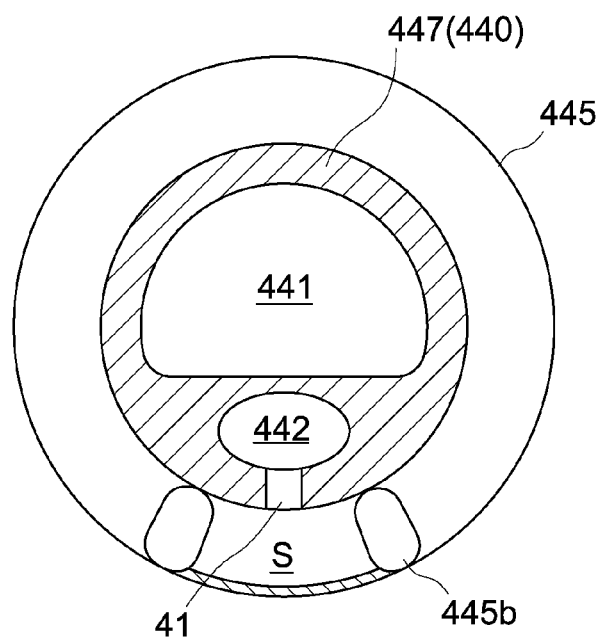
FIG. 12 A cross-sectional view taken along the line C-C in FIG. 10.

FIGS. 10 to 12 are figures showing the configuration including the second end 440b of the tube body 447. FIG. 10 is a plan view. FIG. 11 is a cross-sectional view taken along the line B-B in FIG. 10. FIG. 12 is a cross-sectional view taken along the line C-C in FIG. 10.

The suction inlet 41 is opened in a radial direction of the intubation tube 440. Furthermore, the suction inlet 41 is placed in such a manner that the suction inlet 41 would face an inner surface of the dorsal part of the patient's respiratory tract when the intubation tube 440 is inserted into the respiratory tract of the patient in a supine position. This enables the suction inlet 41 to aspirate the sputum accumulated at the lower part of the respiratory tract. In addition, the second passage 442 is not opened to the second end 440b; and it may be configured to aspirate the sputum only from the suction inlet 41.

The balloon 445 is provided on an outer periphery of the intubation tube 440 and is capable of being in close contact with the patient's respiratory tract. That is, the balloon 445 may dilate in the patient's respiratory tract, to place the intubation tube 440 in a predetermined position inside the respiratory tract. The balloon 445 includes the delivery outlet 443a which communicates with the third passage 443. The balloon 445 would be dilated with the air sent into the balloon 445 from the third passage 443 through the delivery outlet 443a. With the balloon 445 bridging a space between the intubation tube 440 (tube body 447) and the respiratory tract, it would be possible to prevent leakage of the air being sent into the respiratory tract by the artificial ventilator 2.

Figure 13:
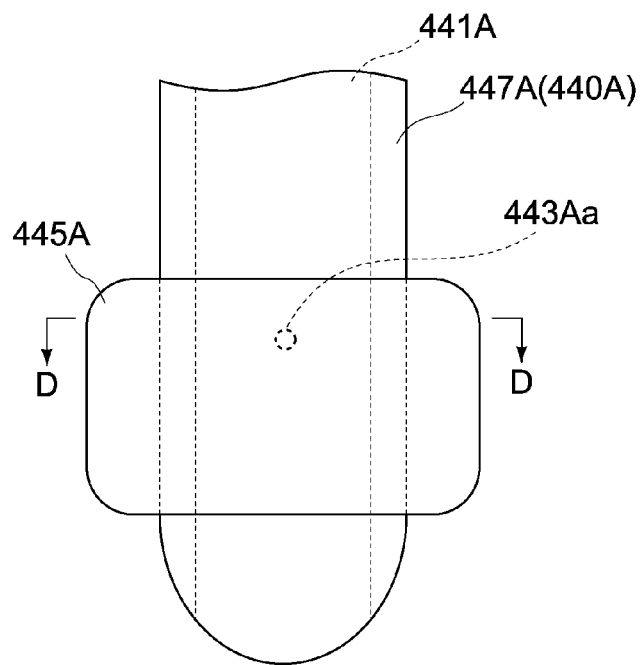
FIG. 13 A plan view of an intubation tube and a balloon of a reference example.
Figure 14:
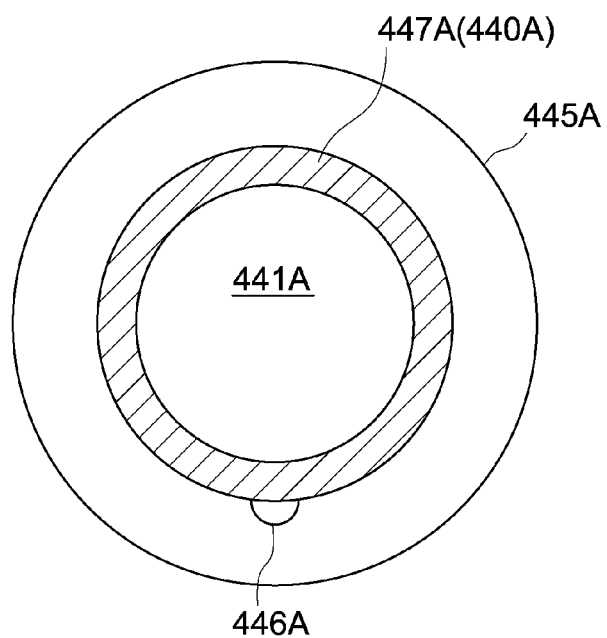
FIG. 14 A cross-sectional view taken along the line D-D in FIG. 13.

Now, FIGS. 13 and 14 are figures showing a configuration of an intubation tube 440A (tube body 447A) and a balloon 445A of a reference example. FIG. 13 is a plan view. FIG. 14 is a cross-sectional view taken along the line D-D in FIG. 13. The intubation tube 440A and the balloon 445A have a same configuration as those in a common tracheal intubation tube. That is, in the intubation tube 440A, a first passage 441A to be connected to an artificial ventilator is formed.

The balloon 445A is provided on an outer periphery of the intubation tube 440A; and is formed annularly. In addition, delivery of air to the balloon 445A is made by a balloon dilatation line 446A through a delivery outlet 443Aa. The balloon dilatation line 446A is provided between the balloon 445A and the intubation tube 440A. It is also possible to place the intubation tube 440A in a predetermined position inside the respiratory tract by the balloon 445A of such a configuration. The sputum being produced in the patient's respiratory tract would be dammed by the balloon 445A; and would be accumulated in a space surrounded by, the inner surface of the respiratory tract, the balloon 445A, and the intubation tube 440A.

On the other hand, the balloon 445 according to this embodiment includes an annular part 445a and a structured part 445b. The annular part 445a is provided annularly on an outer periphery of the intubation tube 440. The annular part 445a has a same configuration as that in the balloon 445A of the reference example; and is placed on, for example, the first end 440a side of the suction inlet 41. The structured part 445b is, for example, a pair of structures extending from the annular part 445a, extending along the longitudinal direction of the intubation tube 440; the pair of structures being placed opposite each other across the suction inlet 41. The structured part 445b forms a space S facing the suction inlet 41.

When the intubation tube 440 is placed in the patient's respiratory tract, the space S forms a space surrounded by the inner surface of the respiratory tract, the annular part 445a, the structured part 445b and the intubation tube 440. Therefore, with the structured part 445b serving as side walls, the space S may be formed narrower than the space of the reference example, which is the space where the sputum would be accumulated. This allows the sputum to flow in a concentrated manner.

This allows the suction inlet 41, facing the space S, to aspirate the sputum in a more effective way than has been done in the reference example. Further, since the sputum flows into the space S in a concentrated manner, the suction inlet 41 is configured to be easily blocked by such sputum. This provides the sputum apparatus 3 with high sensitivity for detection of sputum by the measurement unit 7; and this makes it possible to aspirate sputum before a lot of sputum would be produced.

Furthermore, since the sputum would be accumulated in a space between the balloon 445 and the intubation tube 440 and in the space S, the sputum is not likely to arrive at the first passage 441 which is opened to the second end 440b. This may reduce the risk of disturbing the ventilation of the patient.

Moreover, since the third passage 443 of this embodiment is formed inside the intubation tube 440, there is no need to further provide a separate balloon dilatation line or the like. With this configuration, when the balloon 445 is dilated, the balloon would be placed in close contact with the outer periphery of the intubation tube 440. It therefore can provide a configuration which is resistant to leakage of ventilation gas from the artificial ventilator 2.

In addition, not only the third passage 443 but also the first to fourth passages 441 to 444 are integrally formed inside the intubation tube 440. Therefore, with the intubation tube 440 of this embodiment, as compared to a configuration having a plurality of independent lines or the like, it makes it possible to lessen risk of infection to the patient, reduce invasiveness, and improve safety.

Further, the intubation tube 440 of this embodiment is connectable to a common artificial ventilator 2 which is applied to tracheal intubation. That is, the artificial ventilation system 1 may be realized by connecting the sputum apparatus 3 to the artificial ventilator 2 which has already been introduced in a medical institution or the like; without need of a dedicated artificial ventilator. This makes it possible to reduce the cost for introducing the artificial ventilation system 1.

Moreover, it is possible to perform intubation of the intubation tube 440 in the same manner as that of a common intubation tube, so it may not need special procedures. This makes it possible to introduce the artificial ventilation system 1 smoothly and safely.

Second Embodiment

Figure 15:
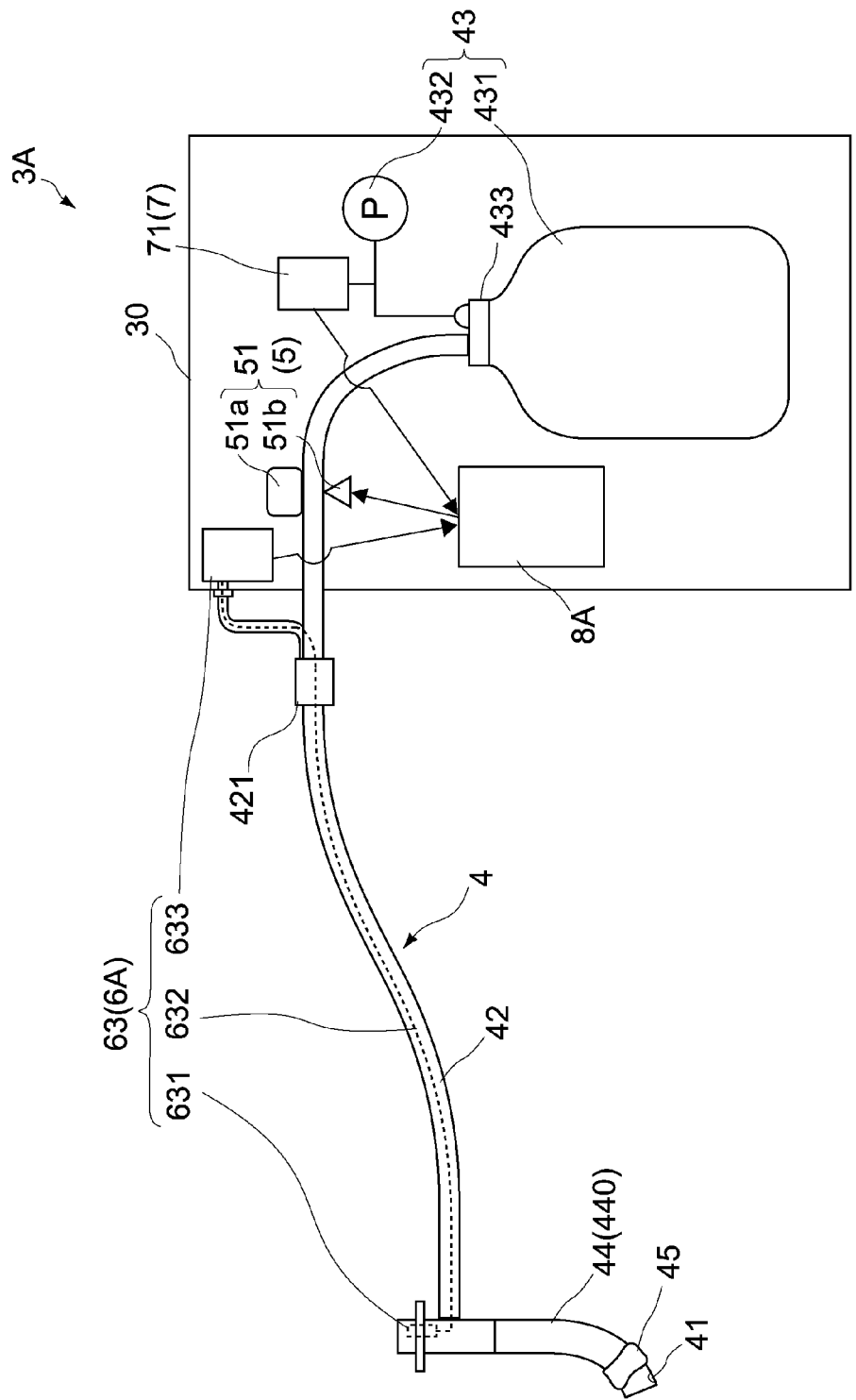
FIG. 15 A schematic diagram of a sputum apparatus according to a second embodiment of the present invention.
Figure 16:
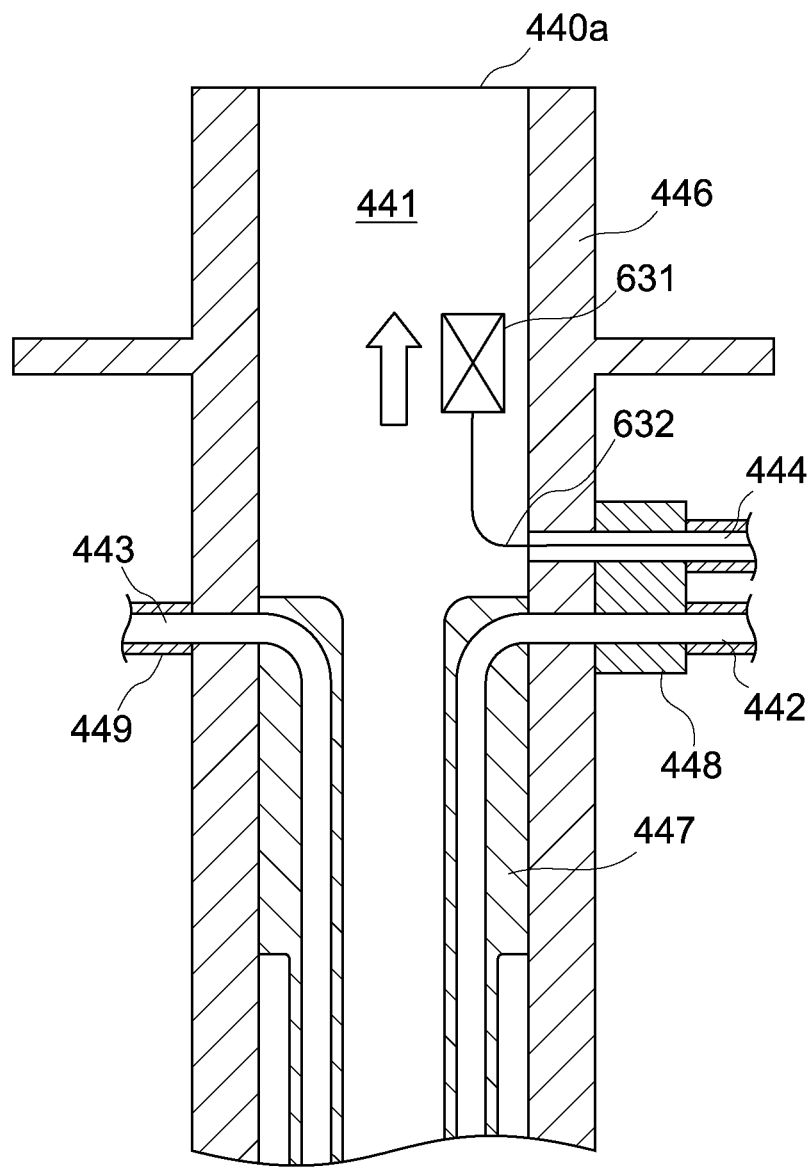
FIG. 16 A sectional view of main component of a tracheal tube (intubation tube) shown in FIG. 15.

FIGS. 15 and 16 are figures showing a sputum apparatus according to a second embodiment of the present invention.

FIG. 15 is a schematic diagram corresponding to FIG. 2. FIG. 16 is a sectional view of main component of an intubation tube, corresponding to FIG. 8. Hereinafter, the components which are different from those of the first embodiment will be mainly described. The components similar to those of the above-described embodiment will be designated by the same reference symbols as those used in the above-described embodiment; and the description of such components will be simplified or omitted.

An artificial ventilation system including a sputum apparatus 3A according to this embodiment may be applied to a process of liberating the patient from artificial ventilation (weaning), in addition to the serious condition in which the patient is unable to breathe spontaneously. The term "weaning" herein means a process of gradually increasing the patient's spontaneous breathing from a state of being fully artificially ventilated; and eventually removing the artificial ventilator. When the patient starts to breathe spontaneously in the process of weaning, the air in the first passage 441 of the insertion part 44 would be directly taken up into the patient's lung during the inspiratory phase. Because of this, an increase in an inner pressure of the first passage 441 would become reduced, as compared to the increase during the artificially-ventilated state. As a result, it may be no longer possible to detect such distinct fluctuations in pressure in the intubation tube 440 as those shown in FIG. 5. Consequently, at the time of weaning, it is difficult for the pressure sensor 61 alone to determine the patient's respiratory status.

In view of this, a detection unit 6A of the sputum apparatus 3A of this embodiment has a flow-direction sensor 63 (sensor). Referring to FIG. 16, the flow-direction sensor 63 is configured to be capable of detecting a flow direction of gas inside the intubation tube 440 (tracheal tube). Since the flow direction of the gas inside the intubation tube 440 may change depending on the patient's respiratory status, the above configuration may allow the detection unit 6A to detect the patient's respiratory status regardless of presence or absence of spontaneous breathing.

The configuration of the flow-direction sensor 63 is not limited in particular, as long as it is capable of detecting the flow of the gas inside the intubation tube 440. Examples of what can be used as the flow-direction sensor 63 include a flow rate sensor (flow sensor) which is capable of detecting the flow direction. Alternatively, it is also possible to employ a configuration to detect the flow direction by using deformation of a diaphragm, or the like, as appropriate.

In this embodiment, the flow-direction sensor 63 has a sensor head 631, a cable 632, and a controller 633. Referring to FIG. 16, for example, the sensor head 631 is placed in the first passage 441 inside the connecting part 446. The sensor head 631 may output an electrical signal corresponding to a flow of a gas. The controller 633 is placed inside the housing 30. The controller 633 performs processing on the signal being input from the sensor head 631, and outputs it to a control unit 8A. The cable 632 is for electrically connecting the sensor head 631 and the controller 633. For example, the cable 632 is configured to run from the sensor head 631 through the fourth passage 444, up to the controller 633 inside the housing 30.

In this embodiment, the control unit 8A determines whether or not it is in the inspiratory phase, based on an output of the flow-direction sensor 63 (controller 633) of the detection unit 6A. Specifically, the control unit 8A can determine that it is in the inspiratory phase, when it detects the flow of the gas (see the arrow in FIG. 16) from the second end 440b on the patient's side of the intubation tube 440 (see FIG. 7) toward the first end 440a; based on the output of the flow-direction sensor 63. Then, if it is determined that it is in the inspiratory phase, the control unit 8A may switch the switching unit 5 to the first state. Thus, an operation for sputum by the sputum apparatus 3A is performed.

As described above, with this embodiment, it is possible to detect the patient's respiratory status, not only during the artificially-ventilated state but also during weaning accompanied by spontaneous breathing of the patient. Therefore, it is possible to use the sputum apparatus 3A during a treatment process from a serious ventilator-dependent condition in the absence of spontaneous breathing, until gradually recovering spontaneous breathing, and until being freed from the artificial ventilator 2. Thus, the automatic aspiration of sputum may be performed over a relatively long term; and this may greatly reduce the burden on the nurses and the like. Further, with the flow-direction sensor 63, it is possible to accurately detect the patient's respiratory status regardless of presence or absence of spontaneous breathing. Therefore, it is possible to avoid the situation that a lot of sputum arises. This enables to perform the aspiration more safely.

Hereinabove, the embodiment of the present invention has been described, but the present invention is not limited thereto, and can be variously modified within the scope without departing from the technical idea of the present invention.

The sputum apparatus according to the above-mentioned embodiments has been described as a sputum apparatus which may be connected to an artificial ventilator being applied to tracheal intubation, but this is not limitative. For example, it is possible to provide the sputum apparatus to be connected to an artificial ventilator that is applied to tracheotomy. In this case, the tracheal tube may have a configuration corresponding to a tracheal cannula; and may also have a configuration including the first to fourth passages.

Further, although it has been described that the first to fourth passages are integrally formed in the intubation tube, it is not limited thereto. Each of the passages, or some of the passages, may be made of a separate tube and the like.

Still further, the sputum apparatus may also have an alarm unit which notifies an abnormal state of aspiration. For example, the alarm unit may have a speaker, or the like, to give an alarm to the nurses and the like in cases such as: when it cannot finish the aspiration as it cannot confirm the inflow of the inspiratory air even after continuing the aspiration over three seconds. In addition, the alarm unit may also have a configuration of an LED lamp which makes an alarm by lighting, a display, or the like.

Still further, the sputum apparatus may also have a notification unit which notifies the time for replacement of the container. For example, the notification unit may be made up of an LED lamp and the like; which may be configured to notify that it is the time for the replacement, by lighting if more than a predetermined value of sputum accumulated in the container 431. Alternatively, the notification unit may include a display which displays an indication that it is the time for the replacement; a speaker which notifies by a voice; or the like. In addition, in cases where the sputum apparatus has the alarm unit, the notification unit may be made up of the same speaker, LED lamp, display, or the like, as that of the alarm unit.

Still further, although it has been described that the measurement unit has a pressure sensor, it is not limited thereto. For example, the measurement unit may have a flowmeter to measure the flow rate of the expired air. In addition, the position of the pressure sensor is not limited to that between the container and the negative-pressure source. For example, the pressure sensor may be placed inside the container or on the cap portion of the container. Alternatively, it is also possible to place the pressure sensor in the suction tube between the switching unit and the container. Since the pressure at the position between the switching unit and the container is substantially the same as the pressure inside the container, this configuration may also enable the pressure sensor to measure the pressure in the accommodating part (inside the container).

Still further, the flow-direction sensor 63 of the second embodiment is not limited to the above-described configuration. For example, the sensor head and the controller may be formed integrally, and may be placed inside the intubation tube 440. Furthermore, running path of the cable 632 is not limited to that passing through the fourth passage 444, but may be one running separate from the suction tube 42. In this case, the suction line 4 may not necessarily have the fourth passage 444.

The configuration of the detection unit is not limited to that having one of the pressure sensor and the flow-direction sensor; but may also have both the pressure sensor and the flow-direction sensor. With this configuration, it becomes possible to detect the patient's respiratory state more surely.

Moreover, the configuration of the detection unit is not limited to that having the pressure sensor or the flow-direction sensor; but may also have a carbon-dioxide concentration sensor or the like, configured to be capable of detecting the respiratory status based on the difference in carbon-dioxide concentration between the expired air and the inspiratory air.

Further, the sputum apparatus may have a communication unit to be connected to the artificial ventilator by wired or wireless communication. This may allow the control unit to grasp a ventilation pattern being self-monitored by the artificial ventilator. This may provide a configuration without the pressure sensor of the detection unit, or the like.

Although it has been described that the switching unit has a clamp, the switching unit is not limited thereto; and may be made up of a switching valve, and the like. Such a switching valve may have its valve body forming a part of the suction path for sputum, of the suction line; and may be capable of switching to make the suction inlet communicate with and shut off from the accommodating part. The switching valve is not limited, which may be a fluid valve, or may be an electromagnetic valve. In addition, the configuration of the suction line is this case is not limited to that having a deformable suction tube; and may also be configured with a tubular structure which is difficult to deform.

Although it has been described that the control unit may switch to the first state during expiration phase and check whether the aspiration of the sputum is needed, it may not be necessary to perform this check every expiration phase. For example, it is also possible that the control unit is configured to perform this check once for two detected periods of expiration phase.

Furthermore, after keeping the first state for the first period of time, the control unit may keep the first state, without switching it to the second state. That is, it is also possible to perform the determination of the expiration phase and the aspiration, in a serial manner.

In the embodiments above, the container has been described as a replaceable soft bag, but it is not limited thereto. For example, the container may be unreplaceable, and may be made of a glass bottle or the like. Alternatively, the container may have a configuration in which a soft bag is housed inside a glass bottle or the like.

DESCRIPTION OF REFERENCE SYMBOLS 1 artificial ventilation system
2 artificial ventilator (artificial ventilation unit)
3 sputum apparatus
4 suction line
5 switching unit
6 detection unit
7 measurement unit
8 control unit
41 suction inlet
42 suction tube
43 accommodating part
44 insertion part
51 clamp
61 pressure sensor
63 flow-direction sensor (sensor)
440 intubation tube
431 container
432 negative-pressure source
441 first passage
442 second passage
443 third passage
444 fourth passage
445 balloon
445b structured part
S space

The invention claimed is:
1. A sputum aspirating apparatus comprising:
a housing;
a suction line comprising:
   a tracheal tube for insertion into a patient's respiratory tract;
   a suction inlet opening toward an outer periphery of the tracheal tube and capable of aspirating sputum produced in the patient's respiratory tract;
   a container to accommodate the aspirated sputum, the container capable of being maintained at a negative pressure, wherein the container is placed in the housing; and
   a suction tube connected between the suction inlet and the container, the suction tube being deformable and penetrating the housing;
a clamp capable of switching between a first state and a second state, the first state making the suction inlet communicate with the container, the second state making the suction inlet shut off from the container, the clamp placed in proximity to the suction line and in the housing, the clamp being configured to open and to block the suction line;
a pressure sensor configured to measure pressure inside the container for measuring an amount of an expired air being aspirated into the container based on changing of the pressure inside the container while in the first state, wherein the pressure sensor is placed in the housing;
a flow-direction sensor for detecting a flow direction of gas inside the tracheal tube; and
a CPU/MPU running software that is configured to perform switching the clamp from the second state to the first state during an expiration phase of the patient as indicated by the flow-direction sensor, and keeping the clamp in the first state when an amount of the expired air measured by the pressure sensor is less than a predetermined value, wherein the CPU/MPU running software is placed in the housing;
wherein the suction tube has a connection part connected to the tracheal tube and a branching part placed outside the housing;

wherein the suction line further comprises:
a first passage capable of being connected to an artificial ventilator, the first passage penetrating through first and second ends of the tracheal tube;
a second passage to communicate with the suction inlet, the second passage formed from the suction inlet that is formed in the tracheal tube to the container that is formed in the housing via the suction tube; and
a third passage to communicate with the first passage, the third passage running parallel to the second passage from the connection part of the suction tube to the branching part and connected from the branching part to the housing;
wherein the flow-direction sensor comprises:
a sensor head for outputting an electrical signal corresponding to a flow of a gas, the sensor head placed in the first passage;
a controller for performing processing on the signal that is input from the sensor head, the controller placed in the housing;
and a cable for electrically connecting the sensor head and the controller, the cable placed in the third passage.

2. The sputum aspirating apparatus according to claim 1, further comprising:
a balloon being provided on an outer periphery of the tracheal tube, the balloon being capable of being in close contact with the patient's respiratory tract; and
a fourth passage being formed in the tracheal tube, the fourth passage being capable of sending air to the balloon.

3. The sputum aspirating apparatus according to claim 2, wherein
the suction inlet is opened in a radial direction of the tracheal tube, and
the balloon includes a structured part forming a space facing the suction inlet.

4. The sputum aspirating apparatus according to claim 1, wherein
the container is replaceable, the container being connectable to a negative-pressure source.

5. The sputum aspirating apparatus according to claim 1, wherein the CPU/MPU running software is further configured to perform keeping the clamp in the first state for a first period of time and determining whether or not the amount of the expired air being aspirated is less than the predetermined value, and when the amount of the expired air measured by the pressure sensor is less than the predetermined value, the CPU/MPU running software is configured to further perform keeping the clamp in the first state for a second period of time longer than the first period of time.

6. An artificial ventilation system comprising:
an artificial ventilation unit to ventilate a patient;
a housing;
a suction line comprising:
a tracheal tube for insertion into a patient's respiratory tract;
a suction inlet opening toward an outer periphery of the tracheal tube and capable of aspirating sputum produced in the patient's respiratory tract;
a container to accommodate the aspirated sputum, the container capable of being maintained at a negative pressure, wherein the container is placed in the housing; and
a suction tube connected between the suction inlet and the container, the suction tube being deformable and penetrating the housing;
a clamp capable of switching between a first state and a second state, the first state making the suction inlet communicate with the container, the second state making the suction inlet shut off from the container, the clamp placed in proximity to the suction line and in the housing, the clamp being configured to open and to block the suction line;
a pressure sensor configured to measure pressure inside the container for measuring an amount of an expired air being aspirated into the container based on changing of the pressure inside the container while in the first state, wherein the pressure sensor is placed in the housing;
a flow-direction sensor for detecting a flow direction of gas inside the tracheal tube; and
a CPU/MPU running software that is configured to perform switching the clamp from the second state to the first state during an expiration phase of the patient as indicated by the flow-direction sensor, and keeping the clamp in the first state when an amount of the expired air measured by the pressure sensor is less than a predetermined value, wherein the CPU/MPU running software is placed in the housing;
wherein the suction tube has a connection part connected to the tracheal tube and a branching part placed outside the housing;
wherein the suction line further comprises:
a first passage connected to the artificial ventilation unit, the first passage penetrating through first and second ends of the tracheal tube;
a second passage to communicate with the suction inlet, the second passage formed from the suction inlet that is formed in the tracheal tube to the container that is formed in the housing via the suction tube; and
a third passage to communicate with the first passage, the third passage running parallel to the second passage from the connection part of the suction tube to the branching part and connected from the branching part to the housing;
wherein the flow-direction sensor comprises:
a sensor head for outputting an electrical signal corresponding to a flow of a gas, the sensor head placed in the first passage;
a controller for performing processing on the signal that is input from the sensor head, the controller placed in the housing;
and a cable for electrically connecting the sensor head and the controller, the cable placed in the third passage.

7. A method for operating a sputum aspirating apparatus, the apparatus comprising a housing, a suction line, a clamp, a pressure sensor, a flow-direction sensor, and a CPU/MPU running software; the suction line comprising a tracheal tube for insertion into a patient's respiratory tract, a suction inlet to aspirate the patient's sputum, a container to accommodate the patient's sputum, and a suction tube being connected between the suction inlet and the container, the suction inlet opening toward an outer periphery of the tracheal tube, the container capable of being maintained at a negative pressure, wherein the container is placed the housing, the suction tube being deformable and penetrating the housing; the clamp placed in proximity to the suction line and capable of switching between a first state and a second state, the first state making the suction inlet communicate with the container, and the second state making the suction inlet shut off from the container, the clamp being configured to open and to block the suction line; the pressure sensor configured to measure pressure inside the container for measuring an amount of an expired air being aspirated into the ontainer based on changing of the pressure inside the container, while in the first state, the pressure sensor placed in the housing; and a flow-direction sensor for detecting a flow direction of gas inside the tracheal tube, wherein the suction tube has a connection part connected to the tracheal tube and a branching part placed outside the housing; wherein the suction line further comprises a first passage connected to an artificial ventilation unit, the first passage penetrating through first and second ends of the tracheal tube; a second passage to communicate with the suction inlet, the second passage formed from the suction inlet that is formed in the tracheal tube to the container that is formed in the housing via the suction tube; and a third passage to communicate with the first passage, the third passage running parallel to the second passage from the connection part of the suction tube to the branching part and connected from the branching part to the housing; wherein the flow-direction sensor comprises a sensor head for outputting an electrical signal corresponding to a flow of a gas, the sensor head placed in the first passage; a controller for performing processing on the signal that is input from the sensor head, the controller placed in the housing; and a cable for electrically connecting the sensor head and the controller, the cable placed in the third passage, the method comprising:

switching the clamp from the second state to the first state during an expiration phase of the patient as indicated by the flow-direction sensor, by the CPU/MPU running software;

determining whether or not an amount of the expired air measured by the pressure sensor is less than a predetermined value, by the CPU/MPU running software; and when the amount of the expired air is less than the predetermined value, keeping the clamp in the first state, by the CPU/MPU running software.

8. The method of operating a sputum aspirating apparatus, according to claim 7, further comprising:

keeping the clamp in the first state for a first period of time and aspirating the expired air into the container, after switching the clamp from the second state to the first state, by the CPU/MPU running software;

determining whether or not the amount of the expired air being aspirated is less than the predetermined value, by the CPU/MPU running software; and when the amount of the expired air is less than the predetermined value, keeping the clamp in the first state for a second period of time longer than the first period of time, by the CPU/MPU running software.

* * * * *